US012173354B2

(12) United States Patent
Ogino et al.

(10) Patent No.: US 12,173,354 B2
(45) Date of Patent: Dec. 24, 2024

(54) METHOD OF DETECTING NUCLEIC ACID AND DETECTION REAGENT

(71) Applicant: TOPPAN PRINTING CO., LTD., Taito-ku (JP)

(72) Inventors: Masayuki Ogino, Taito-ku (JP); Yoichi Makino, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 342 days.

(21) Appl. No.: 16/778,618

(22) Filed: Jan. 31, 2020

(65) Prior Publication Data

US 2020/0224253 A1  Jul. 16, 2020

Related U.S. Application Data

(63) Continuation of application No. PCT/JP2018/028598, filed on Jul. 31, 2018.

(30) Foreign Application Priority Data

Jul. 31, 2017 (JP) ................. 2017-148402

(51) Int. Cl.
*C12Q 1/68* (2018.01)
*C12Q 1/6818* (2018.01)
*C12Q 1/6823* (2018.01)
*C12Q 1/6837* (2018.01)
*C12Q 1/6876* (2018.01)

(52) U.S. Cl.
CPC ......... *C12Q 1/6818* (2013.01); *C12Q 1/6823* (2013.01); *C12Q 1/6837* (2013.01); *C12Q 1/6876* (2013.01); *C12Q 2520/00* (2013.01)

(58) Field of Classification Search
None
See application file for complete search history.

(56) References Cited

U.S. PATENT DOCUMENTS

| | | | | |
|---|---|---|---|---|
| 5,843,669 A | * | 12/1998 | Kaiser | |
| 5,846,717 A | * | 12/1998 | Brow | C12Q 1/6823 435/6.1 |
| 6,562,611 B1 | | 5/2003 | Kaiser et al. | |
| 2003/0138829 A1 | * | 7/2003 | Unger | C12Q 1/68 435/6 |
| 2009/0253142 A1 | | 10/2009 | Allawi et al. | |
| 2014/0057259 A1 | | 2/2014 | Allawi et al. | |

FOREIGN PATENT DOCUMENTS

| | | |
|---|---|---|
| JP | 2001-526526 A | 12/2001 |
| JP | 2005-512031 A | 4/2005 |
| JP | 4016050 B2 | 12/2007 |
| JP | 4362150 B2 | 11/2009 |
| JP | 4363988 B2 | 11/2009 |
| WO | WO 2009/117327 A2 | 9/2009 |

OTHER PUBLICATIONS

Robert W. Kwiatkowski, et al., "Clinical, Genetic, and Pharmacogenetic Applications of the Invader Assay", Molecular Diagnosis, vol. 4 No. 4, XP008021845, Dec. 1999, pp. 353-364 (Year: 1999).*
Mallet et al; Biotechniques, vol. 18, 1995, pp. 678-687.*
Ando et al; Journal of Clinical Microbiology, vol. 35, pp. 570-577, 1997.*
Kaiser et al., "A Comparison of Eubacterial and Archaeal Structure-specific 5'-Exonucleases", Journal of Biological Chemistry, vol. 274, No. 30, 1999, pp. 21387-21394.
Ma et al., "RNA Template-dependent 5' Nuclease Activity of Thermus aquaticus and Thermus thermophilus DNA Polymerases", The Journal of Biological Chemistry, vol. 275, No. 32, 2000, pp. 24693-24700.
Wagner et al., "Quantification of alternatively spliced FGFR2 RNAs using the RNA invasive cleavage assay", RNA, 2003, 9, pp. 1552-1561.
Allawi et al., "Quantitation of microRNAs using a modified Invader assay", RNA, 2004, 10, pp. 1153-1161.
Eis et al., "An invasive cleavage assay for direct quantitation of specific RNAs", Nature Biotechnology, vol. 19, 2001, pp. 673-676.
International Search Report issued Oct. 30, 2018 in PCT/JP2018/028598, filed Jul. 31, 2018, (with English Translation) Additional References sheet(s) attached.
Extended European Search Report issued Jun. 8, 2020 in European Patent Application No. 18840699.5.
Robert W. Kwiatkowski, et al., "Clinical, Genetic, and Pharmacogenetic Applications of the Invader Assay", Molecular Diagnosis, vol. 4 No. 4, XP008021845, Dec. 1999, pp. 353-364.
Office Action issued Jul. 5, 2022 in corresponding Japanese Patent Application No. 2019-534524 (with English-language Translation), 8 pages.
Eis et al., "An invasive cleavage assay for direct quantitation of specific RNAs", Nature Biotechnology, Jul. 2001, vol. 19, No. 7, p. 673-676.

* cited by examiner

*Primary Examiner* — Jehanne S Sitton
(74) *Attorney, Agent, or Firm* — Oblon, McClelland, Maier & Neustadt, L.L.P.

(57) ABSTRACT

A method of detecting a nucleic acid including mixing a fluid including a target nucleic acid with a detection reagent including a first enzyme for cleaving a first nucleic acid having a first flap and a second enzyme for cleaving a second nucleic acid such that the target nucleic acid, the first nucleic acid and the second nucleic acid form a complex as a first invasive structure, conducting a first reaction which causes the first enzyme to cleave the first flap of the first invasive structure and produces a third nucleic acid that forms a complex, as a second invasive structure, with a fourth nucleic acid having a second flap, and conducting a second reaction which causes the second enzyme to cleave the second flap of the second invasive structure and produces a cleaved product.

20 Claims, 13 Drawing Sheets

Specification includes a Sequence Listing.

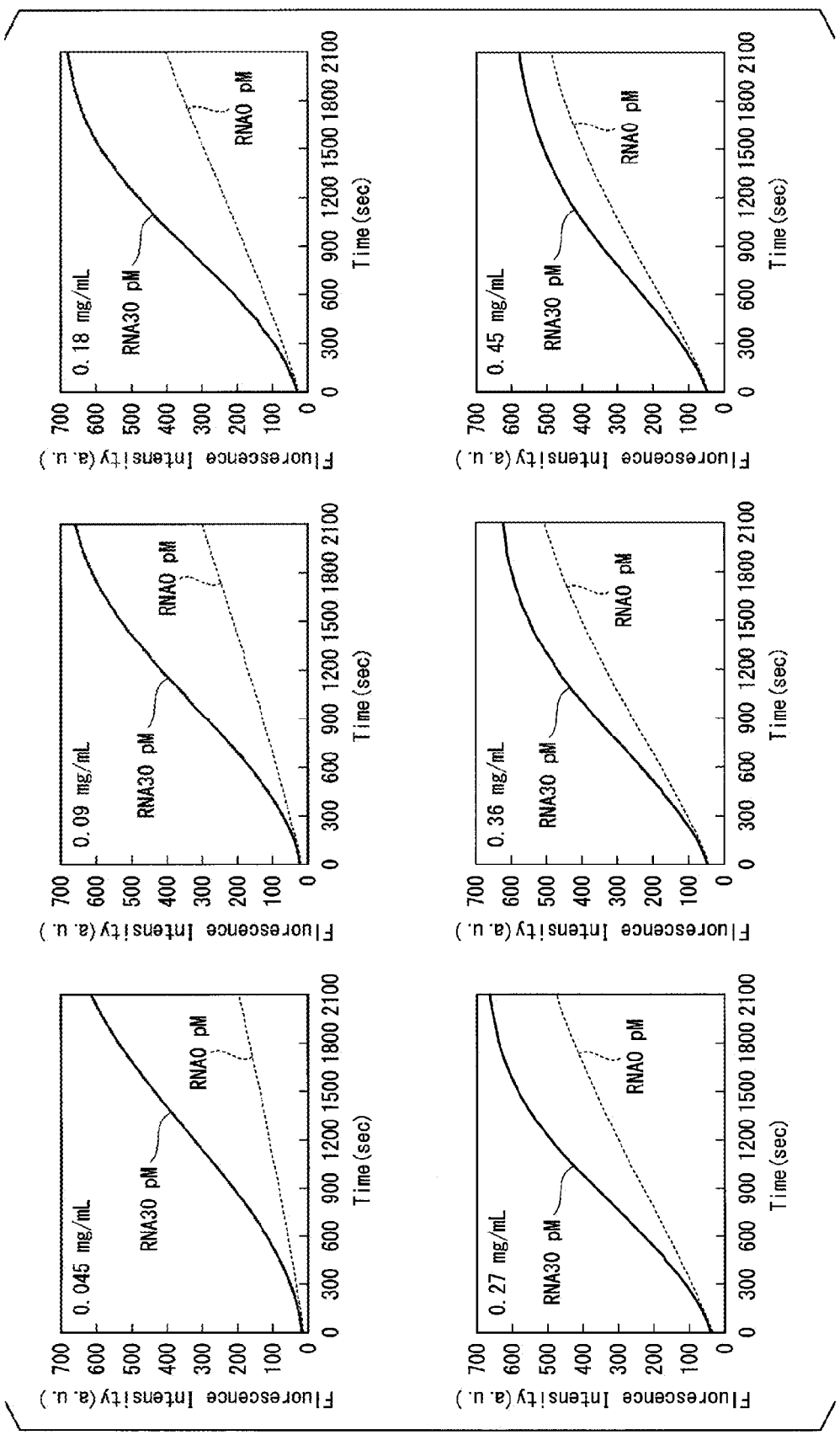

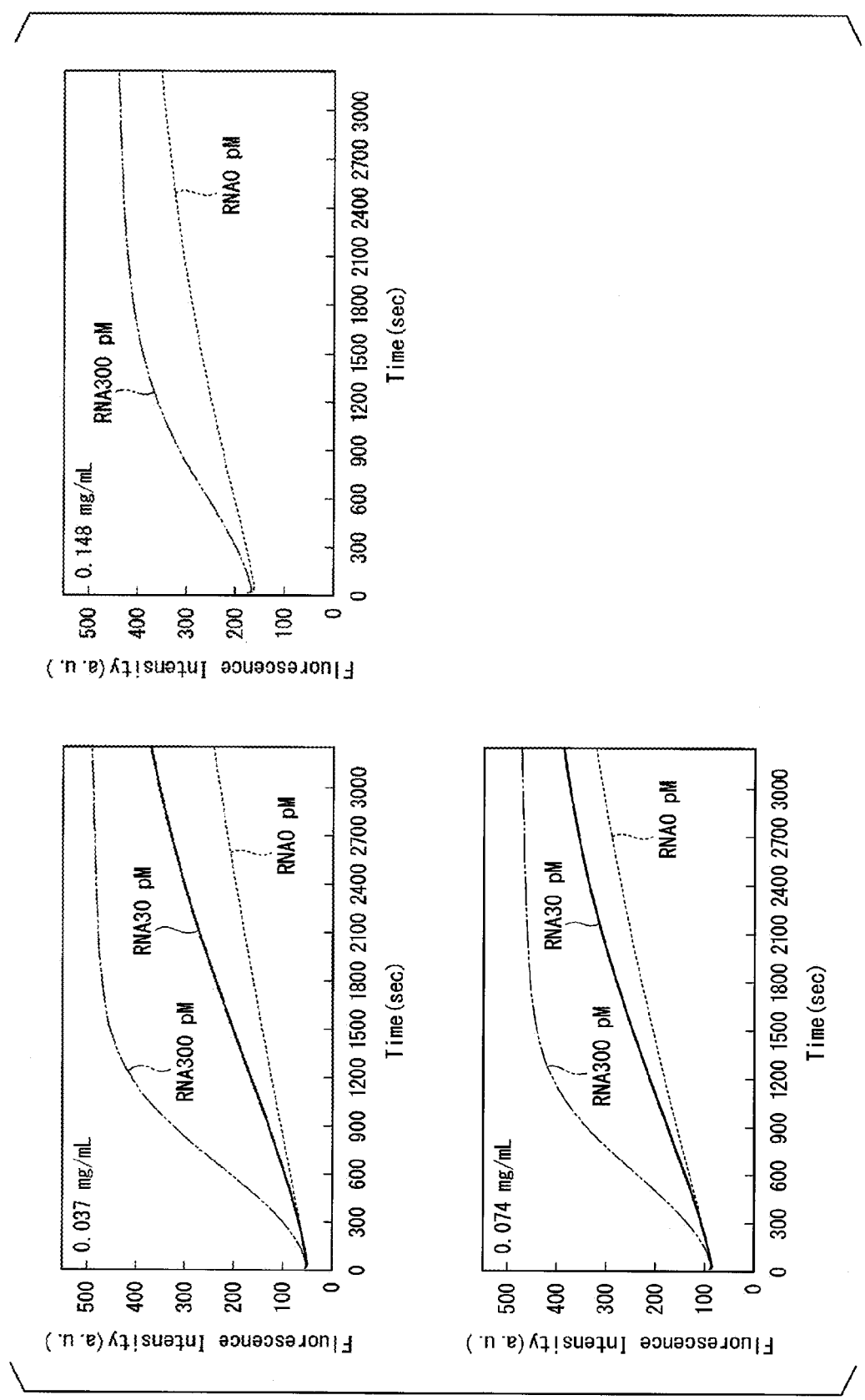

SEQUENCE LISTING

```
<160> NUMBER OF SEQ ID NOS: 5

<210> SEQ ID NO 1
<211> LENGTH: 38
<212> TYPE: RNA
<213> ORGANISM: Artificial Sequence
<220> FEATURE:
<223> OTHER INFORMATION: Target RNA

<400> SEQUENCE: 1
gaagggcaug agcugcguga ugagcugcac gguggagg                            38

<210> SEQ ID NO 2
<211> LENGTH: 24
<212> TYPE: DNA
<213> ORGANISM: Artificial Sequence
<220> FEATURE:
<223> OTHER INFORMATION: First nucleic acid sequence (hybridizing)
<220> FEATURE:
<221> NAME/KEY: misc_feature
<222> LOCATION: (1)..(11)
<223> OTHER INFORMATION: First flap

<400> SEQUENCE: 2
```

```
cgcgccgagg cgcagctcat gccc                                          24

<210> SEQ ID NO 3
<211> LENGTH: 19
<212> TYPE: DNA
<213> ORGANISM: Artificial Sequence
<220> FEATURE:
<223> OTHER INFORMATION: Second nucleic acid sequence (hybridizing)

<400> SEQUENCE: 3
ccaccgtgca rctcatcaa                                                19

<210> SEQ ID NO 4
<211> LENGTH: 11
<212> TYPE: DNA
<213> ORGANISM: Artificial Sequence
<220> FEATURE:
<223> OTHER INFORMATION: Third nucleic acid sequence (hybridizing)

<400> SEQUENCE: 4
cgcgccgagg c                                                        11

<210> SEQ ID NO 5
<211> LENGTH: 33
<212> TYPE: DNA
<213> ORGANISM: Artificial Sequence
<220> FEATURE:
<223> OTHER INFORMATION: Fourth nucleic acid sequence
<220> FEATURE:
<221> NAME/KEY: misc_feature
<222> LOCATION: (1)..(1)
<223> OTHER INFORMATION: terminal T is tagged with 6-fluorescein
<220> FEATURE:
<221> NAME/KEY: misc_feature
<222> LOCATION: (1)..(1)
<223> OTHER INFORMATION: Second flap: F-T
<220> FEATURE:
<221> NAME/KEY: misc_feature
<222> LOCATION: (3)..(4)
<223> OTHER INFORMATION: Quencher (Q) between nucleotides 3 and 4

<400> SEQUENCE: 5
tctagccggt tttccggctg agacctcggc gcg                                33
```

METHOD OF DETECTING NUCLEIC ACID AND DETECTION REAGENT

CROSS-REFERENCE TO RELATED APPLICATIONS

The present application is a continuation of International Application No. PCT/JP2018/028598, filed Jul. 31, 2018, which is based upon and claims the benefits of priority to Japanese Application No. 2017-148402, filed Jul. 31, 2017. The entire contents of all of the above applications are incorporated herein by reference.

REFERENCE TO SEQUENCE LISTING

This application contains a Sequence Listing which has been submitted electronically in ASCII format and is hereby incorporated by reference in its entirety. Said ASCII copy, created on Feb. 25, 2020, is named 526547US_ST25.txt and is 1.66 kb in size.

BACKGROUND OF THE INVENTION

Field of the Invention

The present invention relates to a method of detecting a nucleic acid. More specifically, the present invention relates to a method of detecting the presence or absence of a nucleic acid to be detected in the presence of a detection nucleic acid capable of forming a complex with a nucleic acid sample to be detected and a nucleic acid cleavage enzyme.

Discussion of the Background

There are many methods of accurately and promptly detecting and/or quantifying DNA in genetic diagnoses (PTLs 1 to 3, and NPTLs 1 and 2). Although there are also methods of detecting and/or quantifying RNA, these methods involve reverse transcription or the like which is time consuming. In addition, the reverse transcription reaction may be biased. To enable detection of RNA with fewer operations and in short time, methods involving an isothermal amplification reaction may be used. Among such methods, an invasive cleavage assay (ICA), which uses a nucleic acid cleavage enzyme such as flap endonuclease 1 (FEN-1) or 5'-nuclease, may be effective from the perspective of ease of operation and reaction stability.

In the ICA using FEN-1, the invasive structure on a DNA-DNA double strand is recognized to cause a cleavage reaction at the flap. However, in the case of an RNA-DNA double strand, the cleavage reaction occurs only very slowly. In a similar ICA using the 5'-nuclease that is a nucleic acid cleavage enzyme, the invasive structure on an RNA-DNA double strand can be recognized to cleave the flap. However, in the case of a DNA-DNA double strand, the cleavage activity is reduced. In addition, the flap cleavage activity of the 5'-nuclease for a DNA-DNA double strand is much inferior to that of FEN-1.

Therefore, when flaps of both the DNA-DNA and RNA-DNA double strands are desired to be cleaved in a reaction system where these double strands are mixed, use of only FEN-1 or the 5'-nuclease may reduce the overall cleavage activity.

For example, when a detection signal is desired to be amplified with high efficiency in a detection reaction targeting a nucleic acid, a method in which two types of cleavage reactions are mixed may be used. Specifically, this method includes a first stage of cleaving a flap and a second stage of cleaving a detection nucleic acid which further forms an invasive structure with the cleaved flap, and detecting the cleavage products. After completion of the second stage reaction, the flap can again be used for the first or second stage reaction. Accordingly, signal amplification is accelerated more than when detecting the flap at the first stage.

In this case, if the detection target is DNA and the detection nucleic acid is also DNA, detection can be conducted with an ICA using only FEN-1. However, if the detection target is RNA, the overall cleavage activity may be reduced and the time taken for the detection may increase due to the characteristics of the enzymes mentioned above, irrespective of whether the detection nucleic acid is DNA or RNA. Furthermore, the 5'-nuclease, which has flap cleavage activity to the RNA-DNA mentioned above, may involve side reactions due to misrecognition of the enzyme. If the amount of oxygen is increased in order to reduce the detection time, the frequency of side reactions occurring may increase. Consequently, it may be difficult to make an accurate determination for the results of detection.

To improve such circumstances, there is proposed a method of separating the first and second stages mentioned above which have been performed in the same reaction solution in the conventional art (NPTLs 3 and 4). Specifically, a reaction solution for progressing only the first stage is prepared. The reaction solution is comprised of the 5'-nuclease as a nucleic acid cleavage enzyme, a nucleic acid as target RNA, and two types of oligo DNA required for forming an invasive structure. This method is designed to progress a first stage to some extent, followed by adding a detection nucleic acid simultaneously with the oligo RNA which is termed an arrester oligo as a second stage to minimize side reactions due to misrecognition of the enzyme.

PTL 1: JP 4016050 B
PTL 2: JP 4362150 B
PTL 3: JP 4363988 B
NPTL 1: The Journal of Biological Chemistry, 1999, 274, 21387-21394
NPTL 2: The Journal of Biological Chemistry, 2000, 275, 24693-24700
NPTL 3: RNA, 2003, 9, 1552-1561
NPTL 4: RNA, 2004, 10, 1153-1161

SUMMARY OF THE INVENTION

According to an aspect of the present invention, a method of detecting a nucleic acid includes mixing a fluid including a target nucleic acid with a detection reagent including a first enzyme for cleaving a first nucleic acid having a first flap and a second enzyme for cleaving a second nucleic acid such that the target nucleic acid, the first nucleic acid and the second nucleic acid form a complex as a first invasive structure, conducting a first reaction which causes the first enzyme to cleave the first flap of the first invasive structure and produces a third nucleic acid that forms a complex, as a second invasive structure, with a fourth nucleic acid having a second flap, and conducting a second reaction which causes the second enzyme to cleave the second flap of the second invasive structure and produces a cleaved product.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 9A is a set of graphs each showing change in fluorescence intensity with time observed in Example 2.

FIG. 9C is a set of graphs each showing change in fluorescence intensity with time observed in Example 2.

DESCRIPTION OF THE EMBODIMENTS

Figure 1:
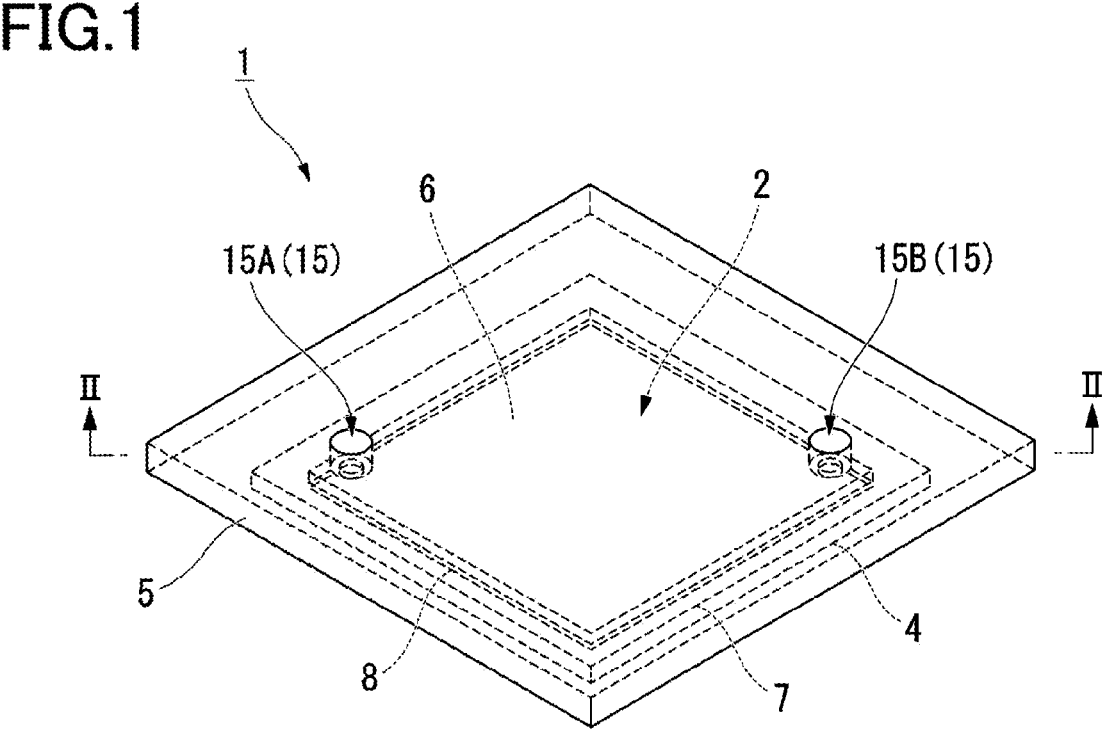
FIG. 1 is a perspective view illustrating a microfluidic device according to the present embodiment.

The embodiments will now be described with reference to the accompanying drawings, wherein like reference numerals designate corresponding or identical elements throughout the various drawings.

First Embodiment

A method of detecting a nucleic acid according to a first embodiment of the present invention will be described.

In the method of detecting a nucleic acid according to the present embodiment, a target nucleic acid is detected in a fluid 20 containing the target nucleic acid.

The method of detecting a nucleic acid of the present embodiment includes a detection reagent mixing step in which a detection reagent (microdroplet) 23 is mixed into the fluid 20.

The detection reagent 23 of the present embodiment contains a first nucleic acid cleavage enzyme and a second nucleic acid cleavage enzyme. The first and second nucleic acid cleavage enzymes contribute to cleaving a specific flap associated with the invasive structure of a specific nucleic acid. The detection reagent 23 may contain, for example, a buffer, a surfactant or the like to facilitate the nucleic acid detection method of the present embodiment. Usually, these reagents are provided being suitably encapsulated.

When nucleic acids are associated with each other in a molecule or between molecules, a part of the base sequences of the nucleic acids becomes hybridized due to formation of a base pair. In the present embodiment, the term flap refers to a portion where either or both of the remaining 3' end and 5' end do not form a base pair. In this case, the portion forming no base pair may have a non-natural structure, such as a fluorescent material or an artificial nucleobase, instead of a usual nucleobase.

In the present embodiment, the invasive structure of nucleic acid refers to a peculiar structure shown in PTLs 1 to 3, NPTLs 1 and 2 or the like. Specifically, the invasive structure of nucleic acid refers to a structure having a flap that is produced when a substrate complex is formed for a target nucleic acid, i.e., a detection target, by hybridization of two types of oligonucleotide probes.

The oligonucleotide probes to be hybridized include a flap probe (FP) and an invasive probe (IP). The flap probe has a base sequence that forms a flap from the 5' end side and a base sequence complementary to the target nucleic acid. The invasive probe hybridizes at a portion that is adjacent to the position where the FP hybridizes. At least one base at the 3' end of the IP has a base sequence overlapping with the 5' portion where the FP hybridizes with the target nucleic acid. If there is an enzyme that can recognize a special structure, such as the invasive structure, for cleavage of the flap, the flap is cleaved.

In the method of detecting a nucleic acid of the present embodiment, the detection reagent mixing step of mixing the detection reagent 23 into the fluid 20 is followed by occurrence of at least two stages of reactions for cleaving the invasive structure.

At a first step, a first nucleic acid having a first flap corresponds to the FP, and a second nucleic acid corresponds to the IP. Hybridization of the first and second nucleic acids with the target nucleic acid forms a complex to thereby form a first invasive structure. The first flap associated with the first invasive structure is cleaved by a first nucleic acid cleavage enzyme, and a third nucleic acid is produced.

At a second stage, the third nucleic acid produced at the first stage corresponds to the IP of a second-stage invasive structure, and a fourth nucleic acid having a second flap and having a base sequence that can hybridize with the third nucleic acid corresponds to the FP. These nucleic acids form a complex to thereby form a second invasive structure. The second flap associated with the second invasive structure is cleaved by a second nucleic acid cleavage enzyme, and a cleaved product is produced. In this case, the fourth nucleic acid has a base sequence that can hybridize with the third nucleic acid, and has a function corresponding to a combination of the target nucleic acid and the FP of the first stage. However, a fifth nucleic acid may be used at the second stage for serving as a target nucleic acid.

The cleaved product can be detected, for example, by comparing migration degrees before and after the reactions by using electrophoresis or the like. The first or fourth nucleic acid contains a fluorescent material having a fluorescent dye and having an absorption wavelength corresponding to the fluorescence wavelength of the fluorescent dye, and a quencher. The presence of a cleaved product may be confirmed based on the luminescence that occurs when the both materials are separated from each other by the cleavage reactions.

By confirming the presence of a cleaved product, the target nucleic acid can be detected in the fluid 20 (target nucleic acid confirmation step).

The method of detecting a nucleic acid of the present embodiment is characterized in that the second nucleic acid cleavage enzyme for the first invasive structure has cleavage activity that is lower than that of the first nucleic acid cleavage enzyme for the first invasive structure, and that the first nucleic acid cleavage enzyme for the second invasive structure has cleavage activity that is lower than that of the second nucleic acid cleavage enzyme for the second invasive structure. These characteristics will be specifically described below.

The term cleavage activity refers to a cleaving performance for an enzyme to recognize an invasive structure and cleave the flap. The cleavage activity can be presented by detecting the amount of cleaved nucleic acid. In the present embodiment, the cleavage activity can be presented by comparing migration degrees before and after the reactions by using electrophoresis, or by measuring the fluorescence intensity attributed to the cleaved product. The cleavage activity can be controlled by the concentration of the enzymes or the reaction conditions. If the reaction conditions and the concentration of the enzymes are fixed, the cleavage activity may hyperbolically increase toward the maximum value, with the increase in concentration of the substrate. If the substrate has a low concentration, the concentration of the substrate may be in proportion to the cleavage activity. For example, the low concentration may be 1 mM or less, or 10 µM or less, or may be 10 nM or less, or 500 pM or less. Therefore, the concentration of an enzyme may be regarded as being approximate to the cleavage activity.

The cleavage activity of the second nucleic acid cleavage enzyme for the first invasive structure may be more than 0% and 90% or less, preferably more than 0% and 80% or less, more preferably more than 0% and 70% or less, and even more preferably more than 0% and 60% or less, relative to the cleavage activity of the first nucleic acid cleavage enzyme for the first invasive structure.

The cleavage activity of the first nucleic acid cleavage enzyme for the second invasive structure may be more than 0% and 90% or less, preferably more than 0% and 80% or less, more preferably more than 0% and 70% or less, and even more preferably more than 0% and 60% or less, relative to the cleavage activity of the second nucleic acid cleavage enzyme for the second invasive structure.

The first nucleic acid cleavage enzyme is capable of recognizing the invasive structure and cleaving the flap. The first nucleic acid cleavage enzyme has cleavage activity for the flap associated with a DNA-DNA double strand structure which is formed when the target nucleic acid is DNA and the FP and the IP are DNA.

The first nucleic acid cleavage enzyme has cleavage activity for the flap associated with an RNA-DNA double strand structure which is formed when the target nucleic acid is RNA and the FP and the IP are DNA.

For example, the first nucleic acid cleavage enzyme may be a nuclease such as polymerase. However, other nucleases may be used. Alternatively, a flap endonuclease that has been modified to recognize the invasive structure of an RNA-DNA double strand structure may be used.

The concentration of the first nucleic acid cleavage enzyme may be 9.0 times or less, preferably 0.10 times or more and 9.0 times or less, more preferably 0.6 times or more and 2.5 times or less, and even more preferably 0.6 times or more and 1.3 times or less, relative to the concentration of the second nucleic acid cleavage enzyme.

If the concentration of the first nucleic acid cleavage enzyme is 9.0 times or less, the detected signal/noise ratio can be increased and detection of the nucleic acid can be facilitated. In particular, the fluorescence intensity of the background may be minimized, while maintaining the fluorescence intensity in the second-stage cleavage reaction.

The concentration of enzyme refers to the concentration expressed by mg/mL.

The second nucleic acid cleavage enzyme is capable of recognizing the invasive structure mentioned above and cleaving the flap. The second nucleic acid cleavage enzyme has higher cleavage activity than the first nucleic acid cleavage enzyme, for the flap associated with a DNA-DNA double strand structure which is formed when the target nucleic acid is DNA and the FP and the IP are DNA.

The second nucleic acid cleavage enzyme has higher cleavage activity than the first nucleic acid cleavage enzyme, for the flap associated with an RNA-DNA double strand structure (e.g., the first invasive structure where RNA is a target nucleic acid) which is formed when the target nucleic acid is RNA and the FP and the IP are DNA. The percentage of activity is characterized in that the percentage is preferably less than 100%, more preferably less than 90%, even more preferably less than 80%, even more preferably less than 70%, even more preferably less than 60%, even more preferably less than 50%, even more preferably less than 40%, even more preferably less than 30%, even more preferably less than 20%, and most preferably less than 10%.

For example, the second nucleic acid cleavage enzyme may be a flap endonuclease. However, other nucleases may be used. Alternatively, a polymerase nuclease that has been modified to recognize the invasive structure of a DNA-DNA double strand structure may be used.

The concentration of the second nucleic acid cleavage enzyme may be 0.1 times or more, preferably 0.1 times or more and 10 times or less, more preferably 0.4 times or more and 1.7 times or less, and even more preferably 0.75 times or more and 1.7 times or less, relative to the concentration of the first nucleic acid cleavage enzyme. The concentration of the second nucleic acid cleavage enzyme may preferably be 0.12 mg/mL or less, more preferably 0.008 mg/mL or more and 0.12 mg/mL or less, and even more preferably 0.03 mg/mL or more and 0.06 mg/mL or less.

If the concentration of the second nucleic acid cleavage enzyme is 0.1 times or more relative to the concentration of the first nucleic cleavage enzyme, noise can be reduced, while reducing the reaction time required for detection. If the concentration of the second nucleic acid cleavage enzyme is 0.12 mg/mL or less as well, noise can be reduced, while reducing the reaction time required for detection.

The method of detecting a nucleic acid of the present embodiment exerts a strong effect in the process of recognizing an invasive structure and detecting the presence or absence of the target nucleic acid based on the occurrence of the cleavage reactions. For example, the detection signal can be amplified by mixing enzymes having different activities into the same reaction system for the nucleic acid structure that is an object to be cleaved, and the noise can be reduced to thereby enhance the signal/noise ratio at the time of detection.

In the methods of detecting a nucleic acid based on the conventional art, unwanted side reactions may occur due to misrecognition of some nucleic acid structure in a nucleic acid cleavage reaction using enzymes. For example, in the target nucleic acid confirmation step mentioned above, a reaction may be caused only by a reagent in spite of containing no target nucleic acid and this reaction may cause fluorescence. Specifically, when the target nucleic acid is RNA, a side reaction of cleaving the flap of a fourth nucleic acid tends to occur in the detection system using one nucleic acid cleavage enzyme, in particular, using the first nucleic acid cleavage enzyme. Therefore, when the additive amount of the enzyme is increased in the reaction system to accelerate the cleavage reaction for the flap for the purpose of reducing the detection time, the side reaction mentioned above may increase. If the additive amount of the first nucleic acid cleavage enzyme is reduced to avoid the side reaction, the time required for the detection may increase.

The side reaction mentioned above may occur similarly when two types of nucleic acid cleavage enzymes are used. The method of detecting a nucleic acid of the present embodiment can minimize the occurrence of the side reaction without increasing the time required for the detection, and can raise the signal/noise ratio at the time of detection. The amount of the first nucleic acid cleavage enzyme in the detection reagent 23 is decreased to minimize the side reaction.

Furthermore, by mixing the second nucleic acid cleavage enzyme into the detection reagent 23, the cleavage activity can be enhanced in the second-stage cleavage reaction (cleavage reaction for the second invasive structure comprised of the third and fourth nucleic acids).

The side reaction is minimized by decreasing the amount of the first nucleic acid cleavage enzyme, and the increase in detection time is prevented by mixing the second nucleic acid cleavage enzyme.

The cleavage activity of the first nucleic acid cleavage enzyme for the fourth nucleic acid is lower compared to the cleavage activity of the second nucleic acid cleavage enzyme for the second invasive structure.

The cleavage activities of the first and second nucleic acid cleavage enzymes for the fourth nucleic acid are both lower compared to the cleavage activity of the first nucleic acid cleavage enzyme for the first invasive structure and the cleavage activity of the second nucleic acid cleavage enzyme for the second invasive structure.

The cleavage activities of the first and second nucleic acid cleavage enzymes for the fourth nucleic acid may both be 80% or less, preferably 60% or less, more preferably 50% or less, even more preferably 40% or less, and most preferably 30% or less, compared to the cleavage activity of the first nucleic acid cleavage enzyme for the first invasive structure and the cleavage activity of the second nucleic acid cleavage enzyme for the second invasive structure.

The concentration of the first nucleic acid cleavage enzyme may be 9.0 times or less, preferably 0.1 times or more and 9.0 times or less, more preferably 0.6 times or more and 2.5 times or less, and even more preferably 0.6 times or more and 1.3 times or less, relative to the concentration of the second nucleic acid cleavage enzyme.

The concentration of the first nucleic acid cleavage enzyme may preferably be 0.27 mg/mL or less, more preferably 0.18 mg/mL or less, even more preferably 0.148 mg/mL or less, even more preferably 0.09 mg/mL or less, even more preferably 0.074 mg/mL or less, even more preferably 0.045 mg/mL or less, and most preferably 0.037 mg/mL or less. The concentration of the second nucleic acid cleavage enzyme may preferably be 0.003 mg/mL or more, more preferably 0.005 mg/mL or more, even more preferably 0.01 mg/mL or more, and most preferably 0.019 mg/mL or more.

The second nucleic acid cleavage enzyme has lower cleavage activity than the first nucleic acid cleavage enzyme, for the flap associated with an RNA-DNA double strand structure (e.g., the first invasive structure where the target nucleic acid is RNA). Accordingly, if the second nucleic acid cleavage enzyme is mixed more into the detection reagent 23, only a small influence may be given to the cleavage activity in the first-stage cleavage reaction that is caused by the first nucleic acid cleavage enzyme (the cleavage reaction for the first invasive structure comprised of the target nucleic acid, and the first and second nucleic acids).

According to the method of detecting a nucleic acid of the present embodiment, the amount of the first nucleic acid cleavage enzyme can be reduced, and cleavage of the second invasive structure by the first cleavage enzyme can be reduced or prevented. Thus, the signal/noise ratio can be raised at the time of detection to more effectively detect the target nucleic acid.

The double strand structure can be formed under conditions of normal temperature, pH, salt concentration, buffer solution, and the like. However, it is preferred to use a solution that is the same as the solution for performing the nucleic acid cleavage reaction. It is preferred that hybridization is performed in a reaction solution containing a salt that produces a buffer effect. The reaction solution may preferably have a pH in the range of 6.5 to 10.0, and particularly preferably in the range of 7.5 to 9.0. The concentration of the salt producing a buffer effect may preferably be in the range of 5 mM to 250 mM, and particularly preferably in the range of 10 mM to 100 mM. The salt producing a buffer effect may be cacodylate, phosphate or tris salt. However, other salts may be used.

The buffer salt may preferably contain alkali metal and/or alkali earth metal. For example, the alkali metal and/or alkali earth metal may preferably be sodium chloride and/or magnesium chloride. The salt concentration of the reaction solution may preferably be in the range of 1 mM to 100 mM, particularly preferably in the range of 5 mM to 50 mM, and even more particularly preferably in the range of 10 mM to 30 mM.

The temperature throughout the reaction may preferably be in the range of 15° C. to 90° C., particularly preferably be in the range of 25° C. to 80° C., and even more particularly preferably in the range of 35° C. to 70° C.

The nucleic acid as a target of detection in the method of detecting a nucleic acid according to the present embodiment is not particularly limited as long as it is DNA or RNA. The nucleic acid may be a natural nucleic acid or a synthetic nucleic acid. Examples of the natural nucleic acid include a genomic DNA, mRNA, rRNA, hnRNA, miRNA and tRNA recovered from living organisms. The synthetic nucleic acid may be a DNA synthesized by a known chemical synthesis method, such as a β-cyanoethyl phosphoramidite method or a DNA solid-phase synthesis method, or may be a nucleic acid synthesized by a known nucleic acid synthesis method, such as PCR, or may be cDNA synthesized by a reverse transcription reaction, or may be other synthetic nucleic acids.

The nucleic acid as a target of detection in the method of detecting a nucleic acid according to the present embodiment is not particularly limited, and may be a nucleic acid extracted from living organisms, such as animals, plants, microbes or cultured cells, or may be a nucleic acid amplified by a nucleic acid amplification reaction. If the amplified product is a double strand nucleic acid, it may be used after being transformed into a single strand by thermal denaturation treatment, chemical denaturation treatment, or the like.

Examples of the nucleic acid amplification reaction include PCR, LAMP, SMAP, NASBA and RCA. Nucleic acid may be extracted from animals or the like by using a known method, such as a phenol/chloroform method.

Advantageous Effects of the First Embodiment

In the method of detecting a nucleic acid of the present embodiment, the signal/noise ratio can be increased at the time of detection without increasing the time required for the detection. This method is particularly highly effective when an RNA is the target nucleic acid.

The method of detecting a nucleic acid of the present embodiment can facilitate detection of a nucleic acid by mixing the detection reagent 23, i.e., microdroplet, into the fluid 20 only once.

Due to the facilitated and prompt RNA detection, tests in hospital can be conducted on the examination date. Thus, a therapeutic policy for medical treatment or dosage can be decided promptly, and accordingly, the patient can be prevented from deteriorating. Moreover, the number of hospital visits can be reduced, which is considered to contribute to coping with medical labor shortages or reducing medical expenses.

Second Embodiment

Figure 2:
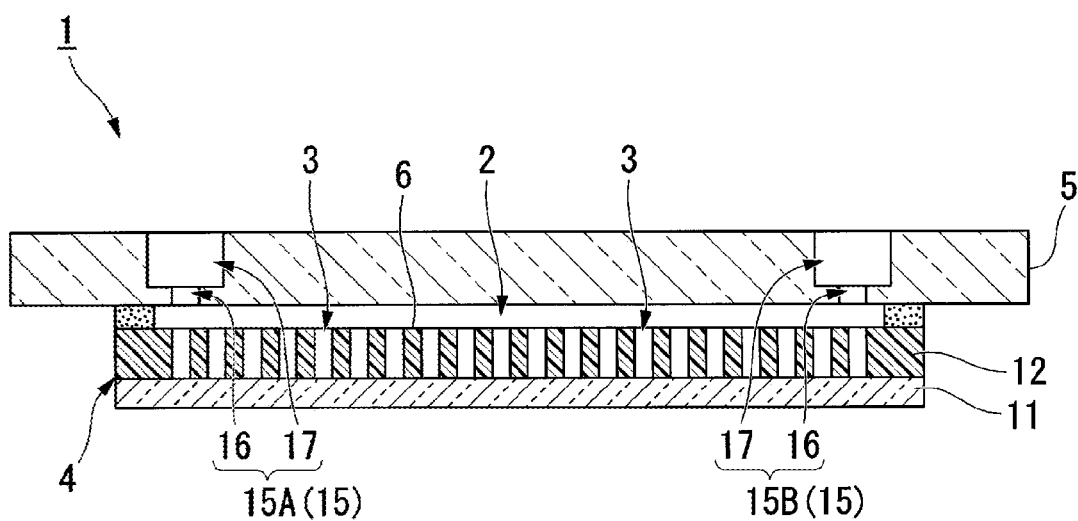
FIG. 2 is a cross sectional view taken along the line II-II of FIG. 1.

Referring to FIGS. 1 to 3, a method of detecting a nucleic acid according to a second embodiment of the present invention will be described. For ease of understanding, dimensions or the like of the components illustrated in the drawings are appropriately adjusted. In the following description, the components common to those already explained are given the same reference signs to omit duplicate description.

The method of detecting a nucleic acid of the second embodiment uses a vessel including a plate which is provided with tubes or wells thereon that are used in a biochemical or molecular biological method based on the conventional art. Besides this vessel, use of microwell arrays having micro-channel structures of various forms is being considered recently. The microwell arrays are formed by using an etching or photolithographic technique used in the technique of fabricating semiconductor circuits. The wells of such a microwell array can be used as chemical reaction vessels for various biochemical or chemical reactions in a microvolume fluid. Numerous microwells are provided on one array, with one microwell containing one detection target. When the presence or absence of a detection target is ensured to be confirmed by the occurrence of fluorescence or the like, only the number of wells where luminescence has been confirmed may have to be counted to quantify the detection target.

The method of detecting a nucleic acid of the second embodiment uses a microwell array as a chemical reaction vessel.

Firstly, an analysis device used in the method of detecting a nucleic acid of the present embodiment will be described. This analysis device is a microfluidic device 1 which is used for a digital counting method that uses liquid biopsy.

FIG. 1 is a perspective view illustrating the microfluidic device 1.

FIG. 2 is a cross sectional view taken along the line II-II of FIG. 1.

FIG. 3 is a set of diagrams each illustrating a principal part of a microwell array 4 of the microfluidic device 1.

Figure 3A:
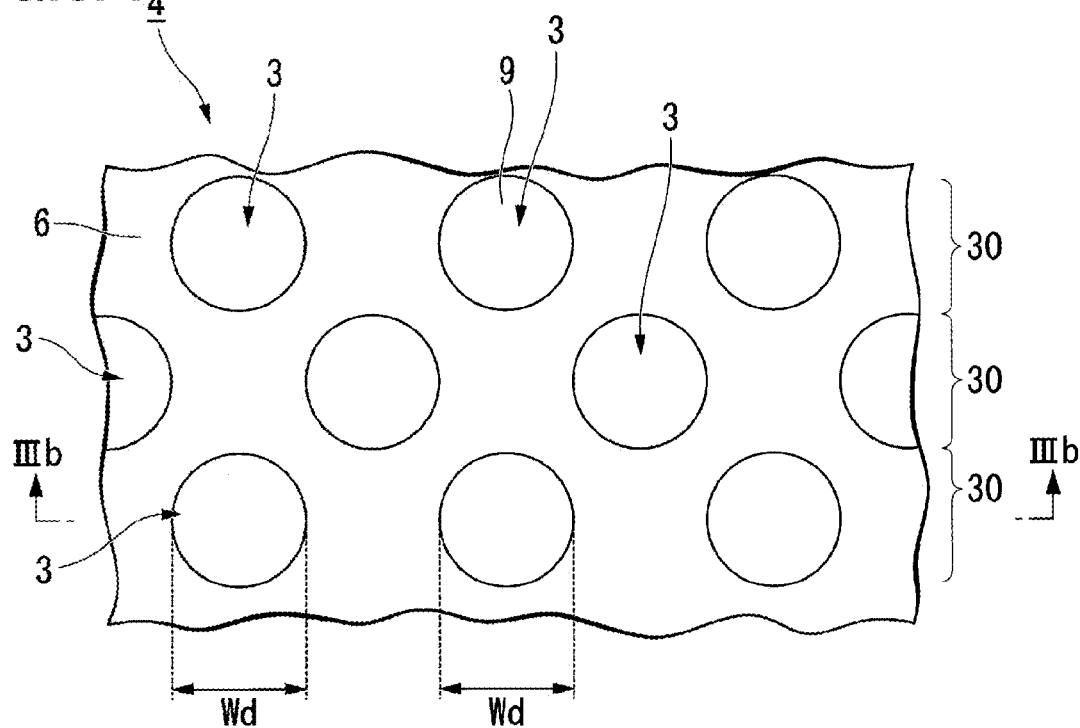
FIG. 3A is a plan view illustrating a principal part of a microwell array of the microfluidic device.
Figure 3B:
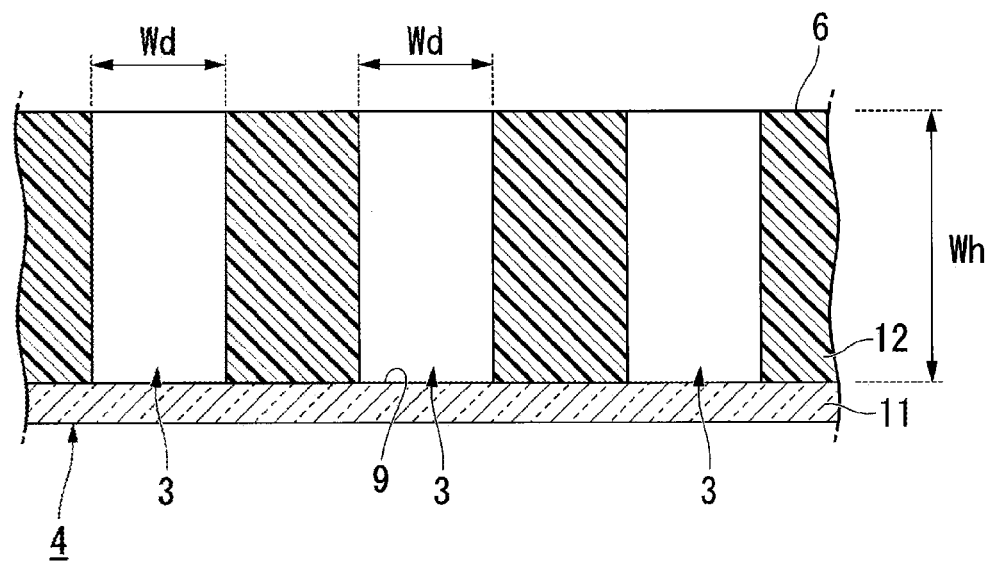
FIG. 3B is a cross-sectional view illustrating a principal part of a microwell array of the microfluidic device, taken along the line IIIb-IIIb of FIG. 3A.

FIG. 3A is a plan view of the microfluidic device 1, and FIG. 3B is a cross-sectional view taken along the line of FIG. 3A. It should be noted that the microfluidic device 1 can be used not only for liquid biopsy, but also for measurement of proteins, DNA, RNA, viral biomolecules, bacteria, or the like.

As shown in FIGS. 1 to 3, the microfluidic device 1 is provided with a microwell array 4 in which a plurality of wells (microspaces) 3 are formed.

As shown in FIGS. 1 and 2, the microwell array 4 includes a plate-like bottom layer 11 and a plate-like wall layer 12 which is overlaid on the bottom layer 11. As shown in FIG. 3A, the plurality of wells 3 of the microwell array 4 are arranged in an array pattern. In FIG. 3A, the plurality of wells 3 are arrayed in the lateral direction (in the horizontal direction as viewed in FIG. 3A) with an interval therebetween. A line of wells 3 arrayed in the lateral direction form a lateral-array well group 30. A plurality of such lateral-array well groups 30 are arranged in the longitudinal direction (in the vertical direction as viewed in FIG. 3A). In lateral-array well groups 30 adjacently located in the longitudinal direction, wells 3 are arranged being offset in the lateral direction so as not to overlap with each other.

The microwell array 4 has a flat surface in which the plurality of wells 3 are open (aperture surface 6). The plurality of wells 3 may be formed across the aperture surface 6 of the microwell array 4. In the present embodiment, however, the plurality of wells 3 are formed in a region (well-forming region 8), excepting a perimeter region 7, of the aperture surface 6 of the microwell array 4. The well-forming region 8 may have any contour. In the present embodiment, the contour is rectangular.

As shown in FIGS. 2 and 3, each well 3 is a hole having a bottom. In the present embodiment, each well 3 is cylindrically formed and has a bottom 9. The shape and size of each well 3 of the microwell array 4 are not particularly limited. For example, if various biochemical reactions are to be induced in microdroplets, each well 3 preferably has a shape and size suitable for containing one to several biomolecules 21 or a carrier. For example, the carrier may be a bead, or the biomolecules 21 as a specimen may be bound to the carrier.

It should be noted that the well 3 may have any shape other than the cylindrical shape. For example, besides the cylindrical shape, the well 3 may have a polygonal shape defined by a plurality of faces (e.g., rectangular parallelepiped, or six- or eight-sided prism), an inverse conical shape, an inverse pyramidal shape (inverse three-, four- five- or six-sided pyramidal shape, or inverse seven or more-sided polygonal pyramidal shape), or the like. The inverse conical or pyramidal shape refers to a shape of the well 3 in which the bottom of the cone or the pyramid serves as an aperture of the well 3. If the well 3 has a reverse conical or pyramidal shape, the vertex, for example, of the cone or the pyramid may be cut off to make the bottom 9 of the well 3 flat. As another example, the well 3 may have a curved bottom 9 which is convex or concave relative to the aperture of the well 3. Also, the well 3 may have a shape, for example, that is a combination of two or more shapes mentioned above.

For example, the well 3 may have a shape a part of which is cylindrical, with the remaining part being reverse conical. When the well 3 has a reverse conical or pyramidal shape, the bottom of the cone or the pyramid is an inlet (aperture) of the well 3. In this case, a part of the reverse conical or pyramidal shape from the vertex may be cut off. In this case, the bottom of each microwell is flat.

As shown in FIG. 3B, the well 3 of the present embodiment has a cylindrical shape with a flat bottom. However, the well 3 may have a curved (convex or concave) bottom. The well 3 having a curved bottom may be applied to the well 3 having a reverse conical or reverse pyramidal shape with a part from the vertex being cut off.

As shown in FIG. 3B, when the well 3 has a cylindrical shape, the well 3 may preferably have a maximum diameter or a height Wh in the range, for example, of 10 nm to 100 µm, more preferably 100 nm to 20 µm, and even more preferably 1 µm to 20 µm in order to encapsulate an aqueous solution containing the biomolecule 21. Considering the amount of the aqueous solution to be contained in the well 3, or considering the preferred ratio or the like between the size of the carrier, such as a bead, to which the biomolecule 21 is adhered and the dimension of the well 3, the dimension of the well 3 is appropriately determined so that one or more biomolecules 21 are contained in one microwell.

The material used for the microwell array 4 may preferably be a material that does not inhibit the enzymatic reactions.

Alternatively, a material that will not inhibit the enzymatic reactions may be applied to the surface of the material of the microwell array 4. For example, a surfactant, a phosphate lipid, other high-molecular-weight compounds, or a mixture thereof may be applied to the surface. As an example of the surfactant, a nonionic surfactant may be used. The nonionic surfactant may be Tween, glycerol, Triton-X100, or the like. Example of the high-molecular-weight compounds include polyethyleneglycol (PEG), DNA, proteins and BSA.

The material to be applied to the surface of the microwell array 4 may be a fluorine-based coating agent or a silicon-based coating agent. By applying such a coating agent to the surface, the surface may be modified to a hydrophobic surface. Application of such a coating agent can minimize adhesion of the solution, buffer, reagent, enzymes, nucleic acid, or other materials contained in the reaction system, and can reduce or prevent erroneous detection.

The detection target in the method of detecting a nucleic acid using the microwell array 4 of the present embodiment may be, for example, a sample, such as blood, collected from a living organism, a PCR product, or the like, or may be an artificially synthesized compound, or other detection targets. For example, if DNA that is a biomolecule 21 is a detection target, the well 3 may have a shape and size suitable for one molecule of the DNA.

The density of the wells 3 in the microwell array 4 may preferably be, for example, in the range of $100,000/cm^2$ to $10,000,000/cm^2$, more preferably $100,000/cm^2$ to $5,000,000/cm^2$, and even more preferably $100,000/cm^2$ to $1,000,000/cm^2$. When the density of the wells 3 is in this range, the operation of encapsulating the aqueous solution as a sample in a predetermined number of wells 3 may be facilitated. In addition, observation of the wells 3 for the analysis of the experimental results may also be facilitated.

For example, in the case of measuring mutations of cell-free DNA, if the ratio of mutations of the detection target to wild-type mutations is about 0.01%, it is preferred, for example, to use 1,000,000 to 2,000,000 wells.

In the microwell array 4, the wells 3 can be formed through a step of forming a hydrophilic or hydrophobic layer by laminating a hydrophilic or hydrophobic material on a substrate, and a step of forming a plurality of wells by drilling the hydrophilic or hydrophobic layer. However, as long as the present embodiment can be realized, the material used for the wells 3 may be the same as the material used for the substrate, and the wells 3 may be formed by molding or cutting.

The microwell array 4 may be formed on a substrate. The substrate may have or may not have electromagnetic wave transmission properties. The electromagnetic waves herein may be an X-ray, ultraviolet ray, visible light, infrared ray, or the like. If the microwell array is formed on a substrate having electromagnetic wave transmission properties, electromagnetic waves can be used for analyzing the results of the experiments performed on the microwell array. For example, fluorescence, phosphorescence or the like emitted as a result of applying electromagnetic waves can be measured from the substrate side. For example, a fluorescence microscope or the like may be used for detecting the fluorescence, phosphorescence or the like. In this case, for example, the electromagnetic waves may be applied from the substrate side or from the inlet side of the wells.

For example, for detecting fluorescence having a peak in the wavelength range of 400 to 700 nm, which is a visible light region, in the microwell array 4, a substrate having good transmission properties at least for visible light in the above wavelength range may be used.

The substrate having electromagnetic wave transmission properties may be, for example, glass, a resin, or the like.

Examples of the resin substrate include an ABS resin, polycarbonate resin, COC (cycloolefin copolymer), COP (cycloolefin polymer), acrylic resin, polyvinyl chloride, polystyrene resin, polyethylene resin, polypropylene resin, polyvinyl acetate, PET (polyethylene terephthalate), PEN (polyethylene naphthalate), and the like. These resins may contain various additives, or a plurality of resins may be mixed.

From the perspective of using fluorescence or phosphorescence for the detection performed for the experimental results, the substrate may preferably be a substrate having substantially no autofluorescence. The term "having substantially no autofluorescence" herein refers to the substrate having no autofluorescence at all with a wavelength used for the detection performed for the experimental results, or the substrate having autofluorescence that is insignificant and does not affect detection performed for the experimental results. For example, autofluorescence which has an intensity that is one-half or less or one-tenth or less or so of the fluorescence of the detection target may be regarded as being insignificant and not affecting detection performed for the experimental results.

For example, the material having electromagnetic wave transmission properties and does not emit autofluorescence at all may be quartz glass. The material that emits insignificantly weak autofluorescence and does not hinder the detection performed for the experimental results may be low fluorescence glass, an acrylic resin, COC (cycloolefin copolymer), COP (cycloolefin polymer), or the like.

The microwell array 4 may have the plurality of wells 3 which have been formed only by injection molding or imprinting resin molding.

The fluorescence used for detecting the biomolecule 21 includes a fluorescent molecule capable of labeling a nucleic acid, a fluorescent bead encapsulating a fluorescent molecule, for example, or fluorescence derived from an intercalator or the like, such as SYBR Green, which specifically enters into the double helix of DNA and emits fluorescence.

The fluorescence emitted from the biomolecule 21 held in each well 3 may be observed from the substrate side of the microwell array 4 by using, for example, a fluorescence microscope. By observing the fluorescence, the number of the wells 3 emitting predetermined fluorescence can be counted to specify the number of target molecules.

For example, the biomolecule 21 may be held as it is in each well 3. Besides, the biomolecule 21 may be treated by a fluorescent labeling agent, which specifically labels a target molecule, before being held in the well 3. Alternatively, the target molecule may be captured by using a bead that specifically recognizes the target molecule, and then the bead may be held in the well 3 and brought into contact with a fluorescent labeling agent that can specifically label the target molecule so that the target molecule can be fluorescently labelled in the well 3.

The substrate may have a thickness that is determined as appropriate. For example, when fluorescence is to be observed from the substrate side by using a fluorescence microscope, the thickness may preferably be, for example, more than 0 mm and 5 mm or less, more preferably more than 0 mm and 2 mm or less, even more preferably more than 0 mm and 0.6 mm or less.

Other than fluorescence, turbidity or the like, for example, may be used for the observation of the biomolecule 21 using the microwell array 4. Turbidity may be measured based on transmission properties of light having a wavelength, for example, of about 400 nm to 1,000 nm.

As long as the advantageous effects of the present invention are achieved, resin for forming a hydrophilic portion (this resin may be termed hydrophilic resin hereinafter) is not particularly limited, but may be a resin whose component comprises molecules having a hydrophilic group that exhibits hydrophilicity. Examples of the hydrophilic group include a hydroxyl group, carboxyl group, sulfone group, sulfonyl group, amino group, amide group, ether group, ester group, and the like.

More specifically, the hydrophilic resin may be selected as appropriate from siloxane polymer; epoxy resin; polyethylene resin; polyester resin; polyurethane resin; polyacrylic amide resin; polyvinyl pyrrolidone resin; acrylic resin such as polyacrylic acid copolymer; polyvinyl alcohol resin such as cationized polyvinyl alcohol, silanolated polyvinyl alcohol, or sulfonated polyvinyl alcohol; polyvinyl acetal resin; polyvinyl butyral resin; polyethylene polyamide resin; polyamide polyamine resin; cellulose derivative such as hydroxy methyl cellulose or methyl cellulose; polyalkylene oxide derivative such as polyethylene oxide or polyethylene oxide-polypropylene oxide copolymer; maleic anhydride copolymer; ethylene-vinyl acetate copolymer; styrene-butadiene copolymer; combinations thereof, or the like. The hydrophilic resin may be a thermoplastic resin, or may be a thermosetting resin, or may be a resin cured by an active energy ray, such as an electronic beam or UV light, or may be an elastomer.

It should be noted that the hydrophilic portion (material of the hydrophilic portion) may have a contact angle of less than 70 degrees as measured using a sessile drop method defined in JIS R3257-1999.

If the substrate is present, the substrate may be ensured to be in intimate contact with the hydrophobic layer. For example, a thermosetting silane coupling agent or the like may be applied to the substrate and thermally cured to form a siloxane polymer to thereby form a hydrophilic layer.

As long as the advantageous effects of the present invention are achieved, resin for forming a hydrophobic portion (this resin may be termed hydrophobic resin hereinafter) is not particularly limited. For example, a resin having a contact angle of 70 degrees or more as measured using a sessile drop method defined in JIS R3257-1999 may be selected as appropriate from novolac resin; acrylic resin; methacrylic resin; styrene resin; vinyl chloride resin; vinylidene chloride resin; polyolefin resin; polyamide resin; polyimide resin; polyacetal resin; polycarbonate resin; polyphenylene sulfide resin; polysulfone resin; fluorine resin; silicone resin; urea resin; melamine resin; guanamine resin; phenolic resin; cellulose resin; combinations thereof, or the like. The hydrophobic resin may be a thermoplastic resin, or may be a thermosetting resin, or may be a resin cured by an active energy ray, such as an electronic beam or UV light, or may be an elastomer.

For example, the hydrophobic portion may be formed of a resist. From the perspective of ease of forming a fine structure, the resist may be a photoresist. For example, the resist may be a photosensitive novolac resin.

As shown in FIGS. 1 and 2, the microwell array 4 is provided with a cover member 5 that configures a channel 2 of the microfluidic device 1 together with the microwell array 4. The cover member 5 is formed into a plate-like or sheet-like shape and disposed facing the aperture surface 6 of the microwell array 4. A gap serving as the channel 2 is defined between the microwell array 4 and the cover member 5.

The cover member 5 includes a plurality of through holes 15 passing therethrough in the thickness direction. The through holes 15 communicate with the channel 2 of the microfluidic device 1 to each serve as an inlet for charging fluid into the channel 2 or as an outlet for discharging fluid therefrom. In the present embodiment, the cover member 5 has two through holes 15A and 15B (first through hole 15A and second through hole 15B). The two through holes 15A and 15B are respectively disposed at two diagonally opposite corners of the rectangular well-forming region 8. Each through hole 15 includes a small hole 16 and a large hole 17 which is larger than the small hole 16 as viewed in a direction in which the through hole is formed.

Advantageous Effects of Second Embodiment

In the method of detecting a nucleic acid of the present embodiment, the signal/noise ratio can be increased at the time of detection without increasing the time required for the detection by mixing the detection reagent 23 into the fluid 20 only once, as in the first embodiment. Furthermore, the detection results can be effectively visualized by using the wells (microspaces) 3.

Figure 4:
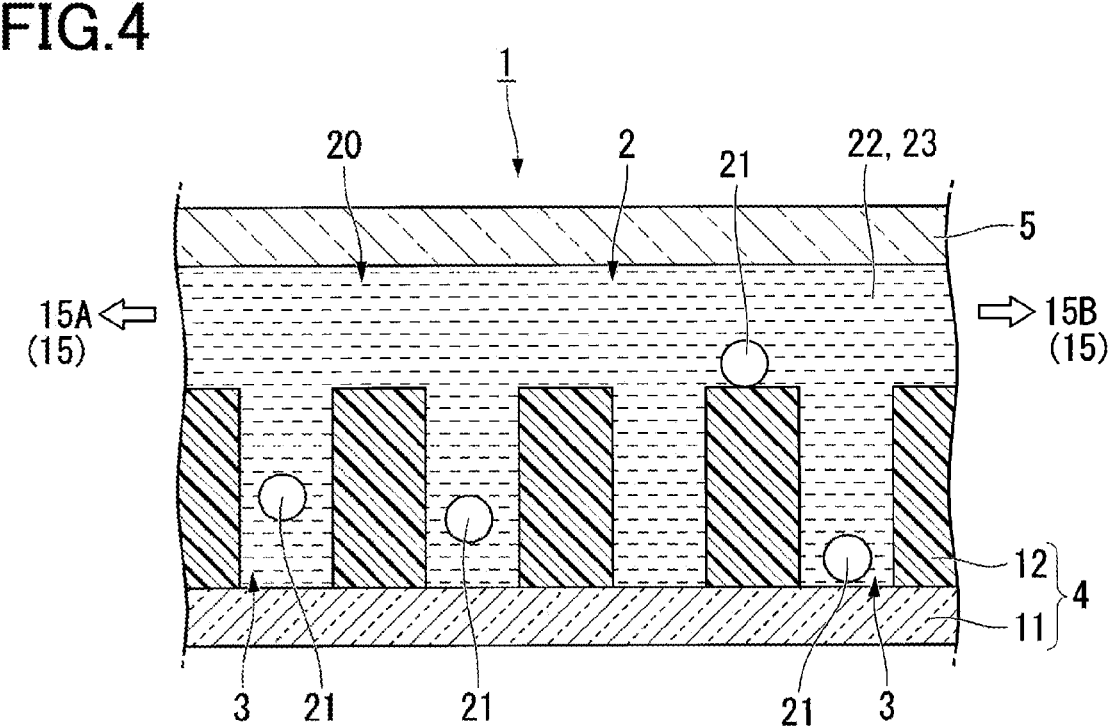
FIG. 4 is a diagram illustrating an example of use of the microfluidic device.
Figure 5:
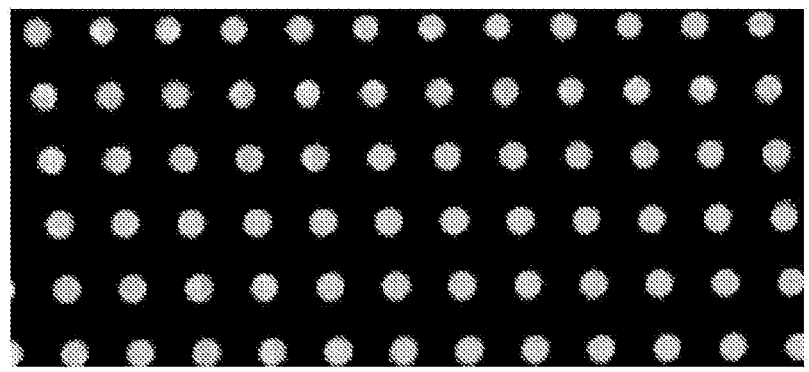
FIG. 5 is an image of fluorescence fields of the microfluidic device.

The following description explains the method of detecting a nucleic acid using the microfluidic device 1 which is provided with the microwell array 4 of the present embodiment. FIGS. 4 and 5 are diagrams illustrating a usage example of the microfluidic device 1.

First, a fluid 20 containing biomolecules 21 as a target nucleic acid, and a sealing liquid are prepared. The fluid 20 comprises the particles 21, a solvent fluid 22 and a detection reagent 23. The sealing liquid, for example, is an oil.

Next, the microfluidic device 1 is placed such that the flow of the fluid 20 and the sealing liquid in the channel 2 is directed in the horizontal direction and that the apertures of the wells 3 are oriented upward in the vertical direction.

Then, the fluid 20 is injected into the channel 2 from the first through hole 15A of the microfluidic device 1 by using a pipette. FIG. 4 shows a state where injection of the fluid 20 has been completed.

After that, the sealing liquid is injected into the channel 2 from the first through hole 15A of the microfluidic device 1 to fill the channel 2 with the sealing liquid. In other words, the fluid 20 in the channel 2 is replaced by the sealing liquid. Thus, the fluid 20 in the wells 3 is sealed by the sealing liquid. After the sealing, the microfluidic device 1 is heated to cause biochemical reactions inside. When a target nucleic acid is contained in the fluid 20, two-stage cleavage reaction is caused for the invasive structure to produce a cleaved product. By detecting the cleaved product, the biomolecules 21 being held in the wells 3 can be detected.

After the reactions, signals, as objects to be measured, are generated in the wells 3 of the microwell array 4. These signals may be fluorescence, luminescence, phosphorescence, and the like. These signals to be measured have wavelength ranges observable as electromagnetic waves, such as visible light, ultraviolet light or infrared light. Accordingly, a detector including a device that can measure such wavelength ranges can be used as a detector of the present embodiment.

Specifically, in the present embodiment, a fluorescence microscope is used as a detector for detecting reactions.

If the microwell array 4 is configured to transmit light, the microfluidic device 1 is disposed so as to be observable from the microwell array 4 side by the fluorescence microscope. FIG. 5 shows an example of an image observed by the fluorescence microscope. In the example shown in FIG. 5, fluorescence is observed by the fluorescence microscope.

In the following, the present invention will be described in detail by way of examples. However the present invention should not be limited by these examples.

EXAMPLES

In the following examples and comparative examples, RNA was detected under the following conditions through an invasive cleavage assay using the sequences shown in Table 1 and the following amount of reagent.

The underlined part of the first nucleic acid shown in Table 1 represents a first flap. The underlined part of the fourth nucleic acid represents a second flap. F in the fourth nucleic acid represents a fluorescent dye and Q represents a quencher.

In the examples, the first and second nucleic acids are hybridized on the target RNA, and a first nucleic acid cleavage enzyme cleaves the first flap to produce the third nucleic acid. The third nucleic acid is hybridized on the fourth nucleic acid and cleaved in this state at the second flap by a second nucleic acid cleavage enzyme and released. Thus, the fluorescent material is separated from the quencher so that fluorescence can be observed.

TABLE 1

| Sequence name | Sequence (5'->3') |
|---|---|
| Target RNA: | GAAGGGCAUGAGCUGCGUGAUGAGCUGC ACGGUGGAGG (SEQ ID NO: 1) |
| First nucleic acid: | CGCGCCGAGGCGCAGCTCATGCCC (SEQ ID NO: 2) |
| Second nucleic acid: | CCACCGTGCARCTCATCAA (SEQ ID NO: 3) |
| Third nucleic acid: | CGCGCCGAGGC (SEQ ID NO: 4) |
| Fourth nucleic acid: | F-TCT-Q-AGCCGGTTTTCCGGCTGAGA CCTCGGCGCG (SEQ ID NO: 5) |

F is 6-fluorescein and Q is Eclipse Quencher.

Example 1

In the present example, a nucleic acid was detected using a detection reagent containing a first nucleic acid cleavage enzyme and a second nucleic acid cleavage enzyme.
(Conditions)

Two types of reaction solutions with different target RNA concentrations were prepared so that the total amount of each reaction solution was 10 μL per one reaction. The reaction solutions contained the target RNA (30 pM, 0 pM), the first nucleic acid (1 μM), the second nucleic acid (1 μM), the fourth nucleic acid (2 μM), 3-morpholinopropanesulfonic acid (pH 7.9, 10 mM), $MgCl_2$ (10 mM), Tween 20 (0.05% v/v), 5'-nuclease (molecular weight: 92290) (0.09 mg/mL) as a first nucleic acid cleavage enzyme, flap endonuclease 1 (molecular weight: 36960) (0.03 mg/mL) as a second nucleic acid cleavage enzyme, and distilled water.
(Procedure)

Each reaction solution was charged into a micro test tube and heated at 65° C. for 60 minutes in a real-time PCR device. Change in fluorescence intensity (excitation: 490 nm, luminescence: 520 nm) during the heating was measured.
(Results)

Figure 6:
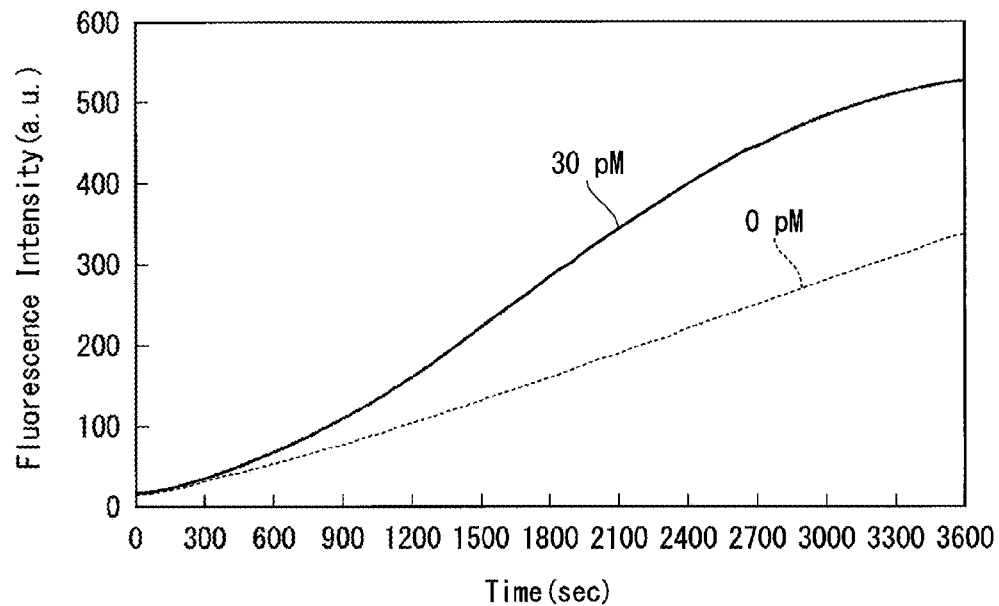
FIG. 6 is a graph showing change in fluorescence intensity with time observed in an example.

The results are shown in FIG. 6. The reaction solution having higher target RNA concentration was observed to exhibit faster rise of fluorescence intensity.

Comparative Example 1

In the present example, the nucleic acid was detected using a detection reagent containing a second nucleic acid cleavage enzyme and not containing a first nucleic acid cleavage enzyme.
(Conditions)

The conditions were the same as in Example 1 except that the reagent did not contain a first nucleic acid cleavage enzyme but contained flap endonuclease 1 (0.03 mg/mL) as a second nucleic acid cleavage enzyme.
(Procedure)

The procedure was the same as in Example 1.
(Results)

Figure 7:
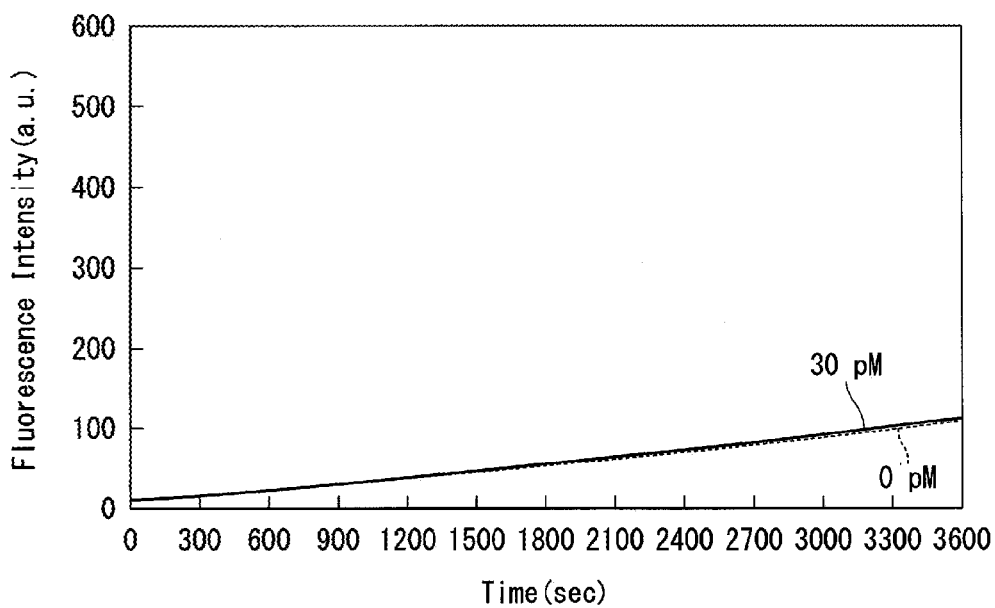
FIG. 7 is a graph showing change in fluorescence intensity with time observed in a comparative example.

The results are shown in FIG. 7. Depending on the target RNA concentration, change in fluorescence intensity was not observed.

Comparative Example 2

In the present example, the nucleic acid was detected using a detection reagent containing a first nucleic acid cleavage enzyme and not containing a second nucleic acid cleavage enzyme.
(Conditions)

The conditions were the same as in Example 1 except that the reagent did not contain a second nucleic acid cleavage enzyme but contained 5'-nuclease (0.09 mg/mL) as a first nucleic acid cleavage enzyme.
(Procedure)

The procedure was the same as in Example 1.
(Results)

Figure 8:
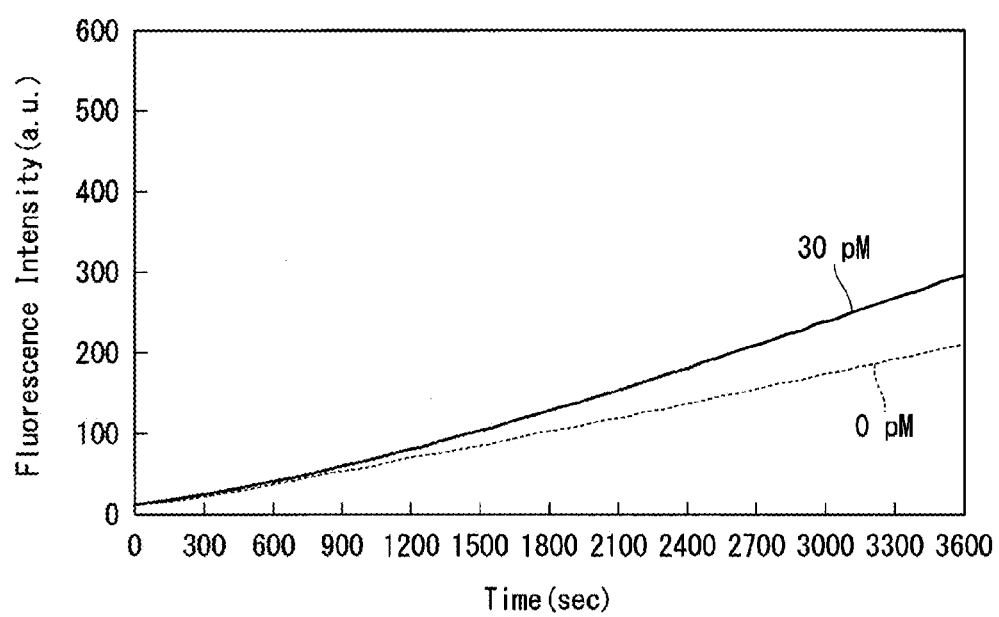
FIG. 8 is a graph showing change in fluorescence intensity with time observed in a comparative example.

The results are shown in FIG. 8. The reaction solution having higher target RNA concentration (30 pM) was observed to exhibit faster rise of fluorescence intensity.

Compared to when only one type of nucleic acid cleavage enzyme was used (Comparative Examples 1 and 2), Example 1 showed higher rise of fluorescence intensity under the conditions in which the target RNA concentration was the same.

The results of Example 1 showed that, when the target nucleic acid was RNA, use of the detection reagent 23 containing both the first and second nucleic acid cleavage enzymes could increase the signal/noise ratio in the detection. Furthermore, the results showed that use of the detection reagent 23 containing both the first and second nucleic acid cleavage enzymes could accelerate rise of fluorescence intensity and prevent detection time from increasing.

Example 2

Figure 9B:
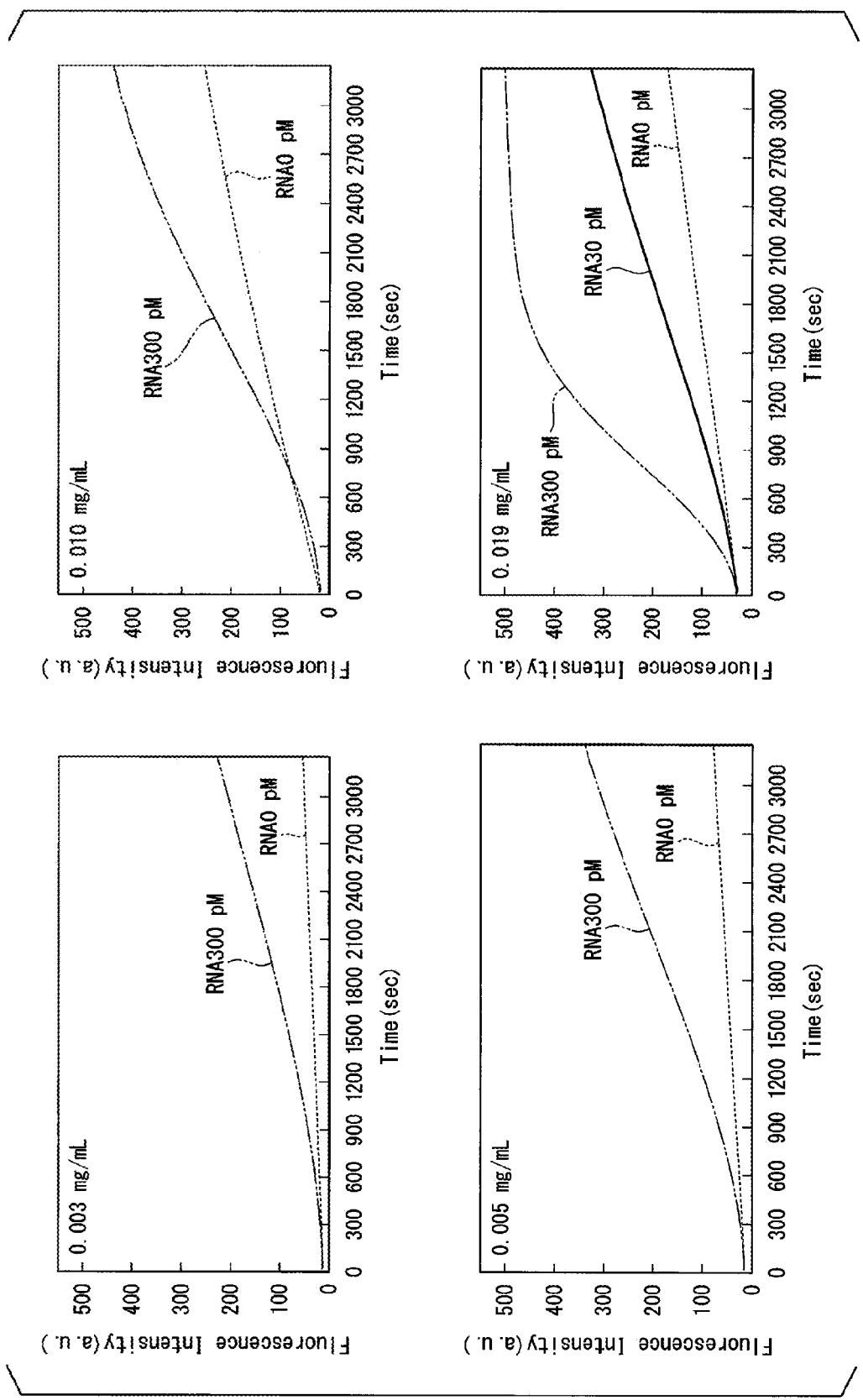
FIG. 9B is a set of graphs each showing change in fluorescence intensity with time observed in Example 2.

In the present example, the influence of the activity ratio between the first and second nucleic acid cleavage enzymes on the signal/noise ratio in the target RNA detection was examined.
(Conditions)
The conditions were the same as in Example 1 except that 13 types of reaction solutions were prepared with the concentration ratios of 5'-nuclease as a first nucleic acid cleavage enzyme in the reaction solutions being respectively 0.10 eq. (0.003 mg/mL), 0.17 eq. (0.005 mg/mL), 0.33 eq. (0.010 mg/mL), 0.63 eq. (0.019 mg/mL), 0.23 eq. (0.037 mg/mL), 1.5 eq. (0.045 mg/mL), 2.46 eq. (0.074 mg/mL), 3.0 eq. (0.09 mg/mL), 4.93 eq. (0.148 mg/mL), 6.0 eq. (0.18 mg/mL), 9.0 eq. (0.27 mg/mL), 12.0 eq. (0.36 mg/mL) and 15.0 eq. (0.45 mg/mL), and the target RNA concentration in the reaction solutions was 30 pM and/or 300 pM. As in Example 1, the second nucleic acid cleavage enzyme was flap endonuclease 1 (0.03 mg/mL).
(Procedure)
The procedure was the same as in Example 1.
(Results)
The results are shown in FIGS. 9A to 9C. When the target RNA concentration was 30 pM and 300 pM, no change in signal rise was observed depending on the concentration ratio of the first nucleic acid cleavage enzyme. When the target RNA concentration was 0 pM, it was confirmed that signal rise was accelerated as the concentration ratio of the first nucleic acid cleavage enzyme increased.

This is because a smaller amount of the first nucleic acid cleavage enzyme minimized the occurrence of side reactions and reduced noise. This is also because mixing of the second nucleic acid cleavage enzyme prevented detection time from increasing. Mixing of the second nucleic acid cleavage enzyme whose activity for the first invasive structure is not high can maintain the detection reaction and increase the signal/noise ratio (difference in fluorescence intensity between the case where the target RNA concentration is 30 pM or 300 pM and the case where the concentration is 0 pM). In particular, a preferred signal/noise ratio is achieved when the concentration ratio of 5'-nuclease as a first nucleic acid cleavage enzyme is 0.10 times, 0.17 times, 0.33 times, 0.63 times, 1.23 times, 1.5 times, 2.46 times, 3.0 times 4.93 times, 6.0 times or 9.0 times, and more preferred signal/noise ratio is achieved when the concentration ratio is 0.10 times, 0.17 times, 0.33 times, 0.63 times, 1.23 times, 1.5 times, 2.46 times, 3.0 times, 4.93 times or 6.0 times.

Example 3

Figure 9D:
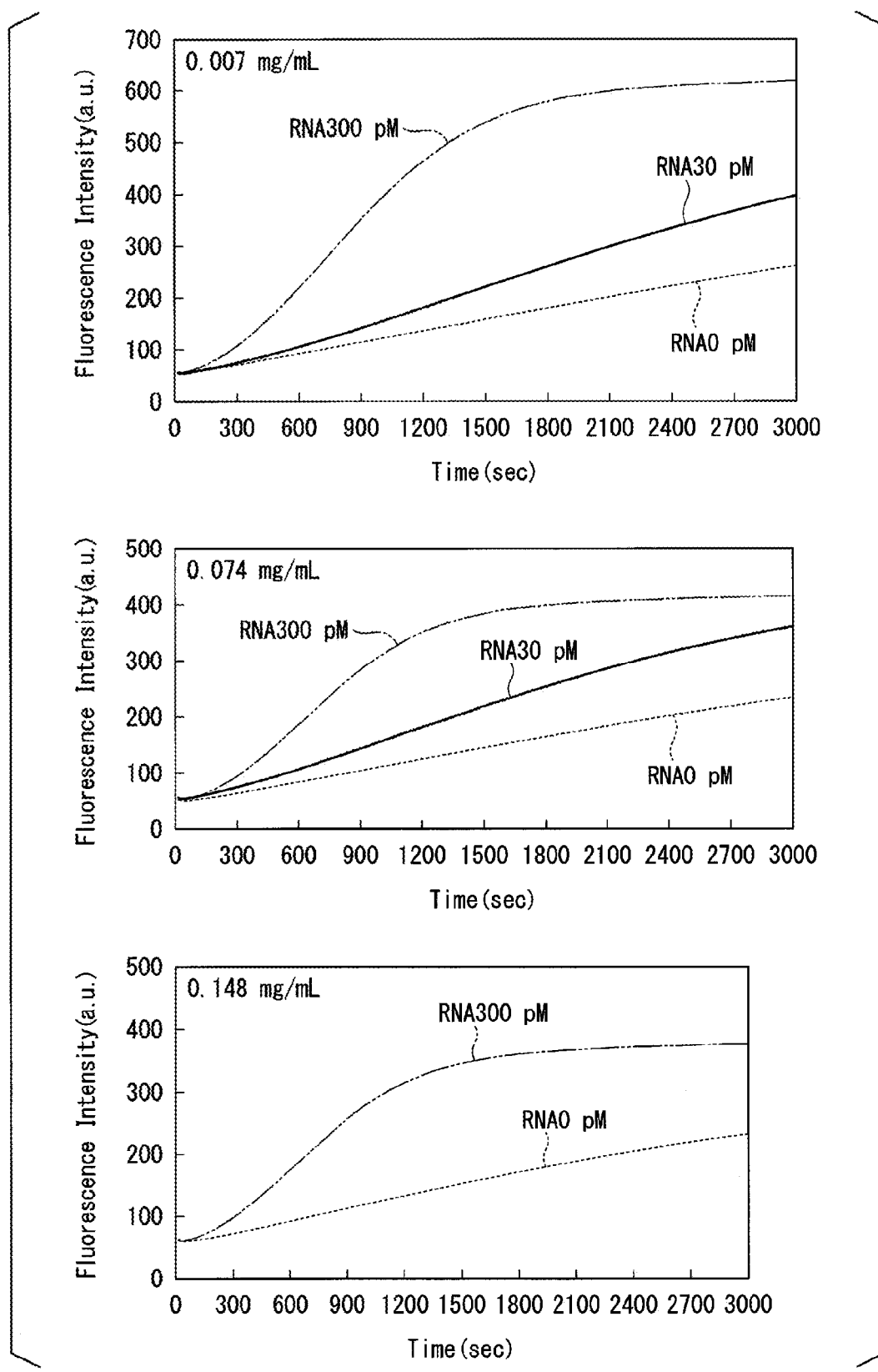
FIG. 9D is a set of graphs each showing change in fluorescence intensity with time observed in Example 3.

In the present example, regardless of the concentration of the second nucleic acid cleavage enzyme, the influence of the activity ratio between the first and second nucleic acid cleavage enzymes on the signal/noise ratio in the target RNA detection was examined.
(Conditions)
The conditions were the same as in Example 1 except that 3 types of reaction solutions were prepared with the concentration ratios of 5'-nuclease as a first nucleic acid cleavage enzyme in the reaction solutions being respectively 0.63 eq. (0.037 mg/mL), 1.23 eq. (0.074 mg/mL) and 2.46 eq. (0.148 mg/mL), and flap endonuclease 1 as a second nucleic acid cleavage enzyme in the reaction solutions was 0.06 mg/mL.
(Procedure)
The procedure was the same as in Example 1.
(Results)
The results are shown in FIG. 9D. When the target RNA concentration was 30 pM and 300 pM, no change in signal rise was observed depending on the concentration ratio of the first nucleic acid cleavage enzyme. When the target RNA concentration was 0 pM, it was confirmed that signal rise was accelerated as the concentration ratio of the first nucleic acid cleavage enzyme increased.

This is because a smaller amount of the first nucleic acid cleavage enzyme minimized the occurrence of side reactions and reduced noise. This is also because mixing of the second nucleic acid cleavage enzyme prevented detection time from increasing. Mixing of the second nucleic acid cleavage enzyme whose activity for the first invasive structure is not high can maintain the detection reaction and increase the signal/noise ratio (difference in fluorescence intensity between the case where the target RNA concentration is 30 pM or 300 pM and the case where the concentration is 0 pM). Results of the above and Example 2 show that, regardless of the concentration of the second nucleic acid cleavage enzyme, good signal/noise ratio can be achieved. In particular, when the concentration ratio of 5'-nuclease as a first nucleic acid cleavage enzyme was 0.63 times, 1.23 times or 2.46 times, a preferred signal/noise ratio is achieved.

Furthermore, when the concentration ratio of 5'-nuclease as a first nucleic acid cleavage enzyme was 0.63 times or 1.23 times, a preferred signal/noise ratio is achieved regardless of the target RNA concentration. Thus, when the concentration of 5'-nuclease as a first nucleic acid cleavage enzyme is 0.6 times or more and 1.3 times or less, the target nucleic acid of various concentrations can be detected at a preferred signal/noise ratio, and when the concentration of the second nucleic acid cleavage enzyme is 0.03 mg/mL or more and 0.06 mg/mL or less, detection can be performed at a more preferred ratio.

Example 3

In the present example, the influence of the activity ratio between the first and second nucleic acid cleavage enzymes on the signal/noise ratio in the target RNA detection was examined. In the present example, experiments were conducted by fixing the concentration of the first nucleic acid cleavage enzyme to 0.63 eq. and varying the concentration of the second nucleic acid cleavage enzyme.
(Conditions)
The conditions were the same as in Example 1 except that 5 types of reaction solutions were prepared so that the concentration ratio of 5'-nuclease as a first nucleic acid cleavage enzyme in the reaction solutions was 0.63 eq., with the concentrations of flap endonuclease 1 as a second nucleic acid cleavage enzyme being respectively 0.008 mg/mL, 0.015 mg/mL, 0.06 mg/mL, 0.12 mg/mL and 0.24 mg/mL, and with the concentrations of 5'-nuclease as a first nucleic acid cleavage enzyme being respectively 0.005 mg/mL, 0.01 mg/mL, 0.037 mg/mL, 0.074 mg/mL and 0.148 mg/mL according to the concentrations of the second nucleic acid cleavage enzyme, and the target RNA concentration in the reaction solutions was 30 pM and/or 300 pM.
(Procedure)

The procedure was the same as in Example 1.
(Results)

Figure 9E:
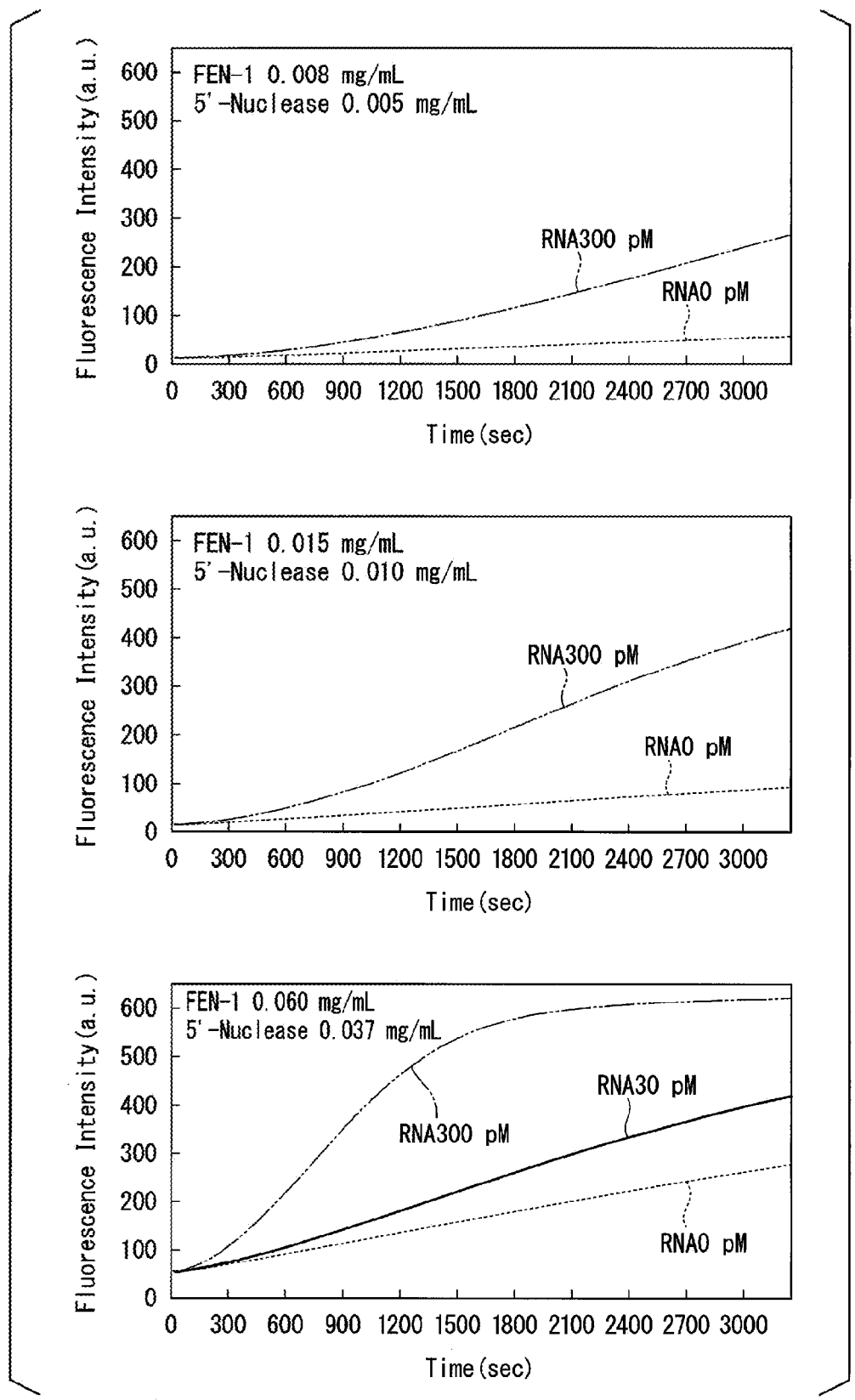
FIG. 9E is a set of graphs each showing change in fluorescence intensity with time observed in Example 4.
Figure 9F:
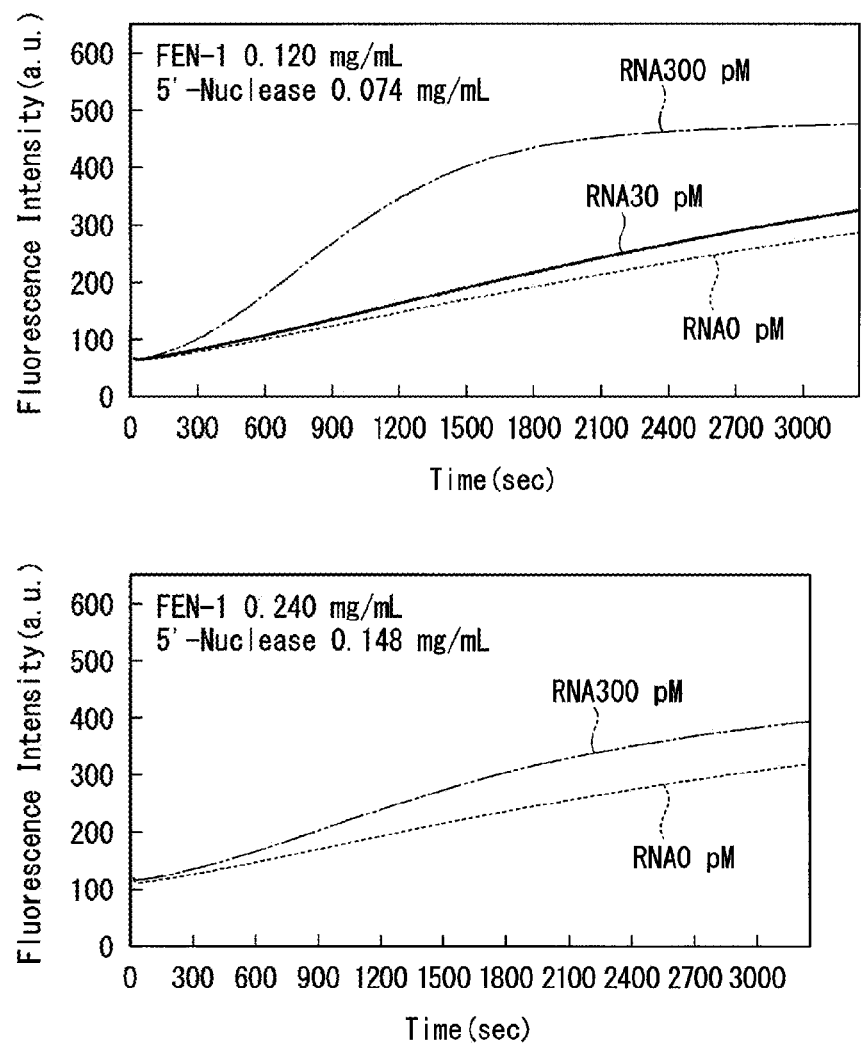
FIG. 9F is a set of graphs each showing change in fluorescence intensity with time observed in Example 4.

The results are shown in FIGS. 9E and 9F. When the target RNA concentration was 30 pM and 300 pM, no change in signal rise was observed depending on the concentration of the second nucleic acid cleavage enzyme. It was confirmed that, when the target RNA concentration was 0 pM, signal rise was accelerated as the concentration of the second nucleic acid cleavage enzyme was increased. However, significant difference was not confirmed when the concentration of the second nucleic acid cleavage enzyme was 0.06 mg/mL or more.

This is because a smaller amount of the first nucleic acid cleavage enzyme minimized the occurrence of side reactions and reduced noise. This is also because mixing of the second nucleic acid cleavage enzyme prevented detection time from increasing. Mixing of the second nucleic acid cleavage enzyme whose activity for the first invasive structure is not high can maintain the detection reaction and increase the signal/noise ratio (difference in fluorescence intensity between the case where the target RNA concentration is 30 pM or 300 pM and the case where the concentration is 0 pM). Results of the above and Example 2 showed that, regardless of the concentration of the second nucleic acid cleavage enzyme, good signal/noise ratio was achieved as long as the concentration ratio of the first and second nucleic acid cleavage enzymes was in a predetermined range. In particular, as can be seen, when the concentration of the second nucleic acid cleavage enzyme is 0.008 mg/mL, 0.015 mg/mL, 0.03 mg/mL, 0.06 mg/mL or 0.12 mg/mL, a preferred signal/noise ratio is achieved, and when the concentration thereof is 0.03 mg/mL or 0.06 mg/mL, a more preferred signal/noise ratio is achieved. However, even when the concentration ratio of the second and first nucleic acid cleavage enzymes was unchanged but the concentrations of the first and second nucleic acid cleavage enzymes were excessively increased, signal/noise ratio was poor and, when the concentration of the second nucleic acid cleavage enzyme was 0.24 mg/mL, no satisfactory signal/noise ratio was obtained.

Example 5

In the present example, the effects of improvement in signal/noise ratio were examined when observing fluorescence signals in the wells 3.
(Conditions)

Reaction solutions were prepared so that the total amount of each reaction solution was 20 μL per one reaction. The reaction solutions contained the target RNA (0 pM, 30 pM), the first nucleic acid (1 μM), the second nucleic acid (1 μM), the fourth nucleic acid (2 μM), trishydroxymethylaminomethane-hydrochloric acid buffer solution (pH 9.0, 10 mM), $MgCl_2$ (10 mM), Tween 20 (0.05% v/v), 5'-nuclease as a first nucleic acid cleavage enzyme with varied concentration ratios (0.045, 0.09, 0.18, 0.27, 0.36, 0.45 mg/mL), flap endonuclease 1 (0.03 mg/mL) as a second nucleic acid cleavage enzyme, and distilled water.

(Procedure)

Each reaction solution was supplied to the first through hole 15A of the microfluidic device 1 and then 80 μl of FC-40 (Sigma) as a sealing liquid that was immiscible with the detection reaction reagent was supplied through the first through hole 15A to distribute the reagent to the individual wells 3 and seal the reagent therein. The microfluidic device 1 was heated on a hot plate at 66° C. for 15 minutes to cause an Invader reaction. Next, fluorescence in the respective micro-holes was detected by using a fluorescence microscope (manufactured by Keyence Corporation) and a NIBA fluorescence filter.
(Results)

Figure 10A:
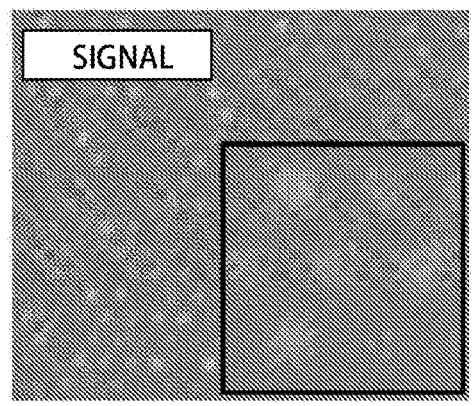
FIG. 10A is an image showing fluorescence fields (signal) of the microfluidic device observed in an example.
Figure 10B:
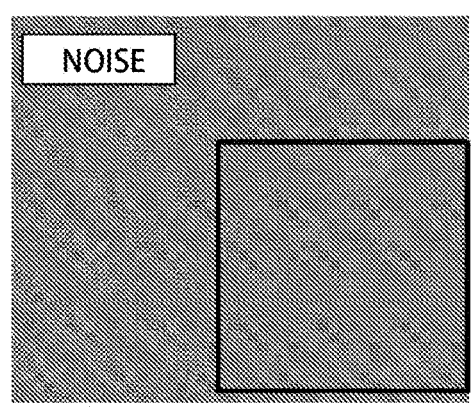
FIG. 10B is an image showing fluorescence fields (noise) of the microfluidic device observed in an example.

The results are shown in FIG. 10. The exposure time was 1,000 msec. FIG. 10A shows the case where the target RNA concentration was 30 pM. Fluorescence signals having intensities that were different from the noise in the wells 3 could be confirmed. FIG. 10B shows the results of the case where the target RNA concentration was 0 pM. As can be seen, the wells 3 have low noise fluorescence intensities.

Comparative Example 3

To examine the degree of side reactions, a reaction solution containing no target RNA was prepared and the behaviors exhibited by the reaction solution were observed. The reaction solution was a mixture of the fourth nucleic acid, the first nucleic acid and 5'-nuclease as a first nucleic acid cleavage enzyme.
(Conditions)

A reaction solution was prepared so that the total amount was 10 μL per one reaction. The reaction solution contained the first nucleic acid (1 μM), the fourth nucleic acid (2 μM), 3-morpholinopropanesulfonic acid (pH 7.9, 10 mM), $MgCl_2$ (10 mM), Tween 20 (0.05% v/v), 5'-nuclease (0.09 mg/mL) as a first nucleic acid cleavage enzyme and distilled water.
(Procedure)

The reaction solution was charged into a micro test tube and heated at 65° C. for 60 minutes in a real-time PCR device. Change in fluorescence intensity (excitation: 490 nm, luminescence: 520 nm) during the heating was measured.
(Results)

Figure 11:
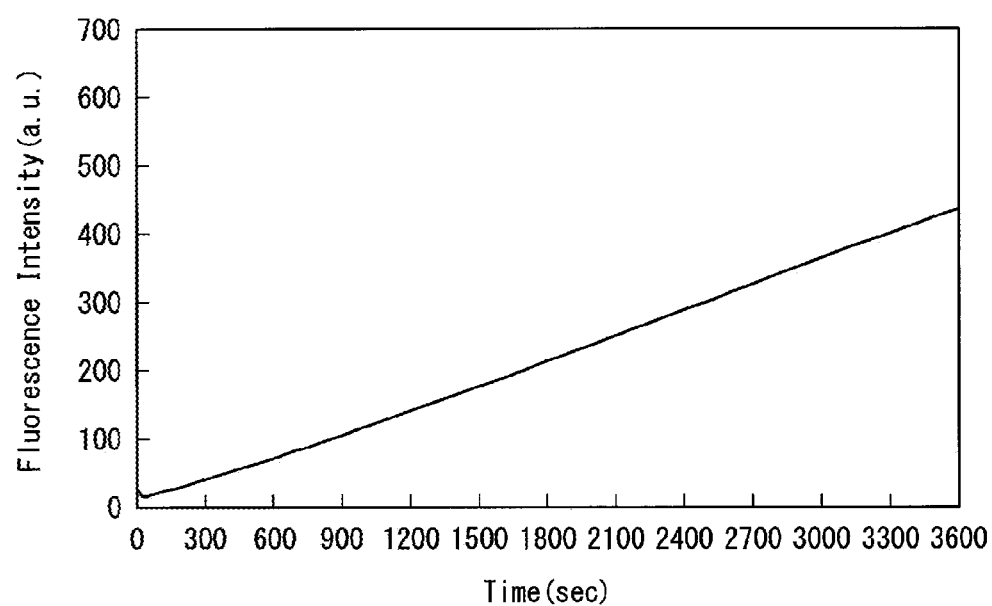
FIG. 11 is a graph showing change in fluorescence intensity with time observed in an example.

FIG. 11 shows the results. In the absence of the target RNA, it was observed that fluorescence intensity increased with time. From these results, it was confirmed that at least the first and fourth nucleic acids contributed to increasing noise (fluorescence intensity increased in the absence of the target RNA).

Comparative Example 4

To examine the degree of side reactions, a reaction solution containing no target RNA was prepared and the behaviors exhibited by the reaction solution were observed. The reaction solution was a mixture of the fourth nucleic acid, the first nucleic acid and FEN-1 as a second nucleic acid cleavage enzyme.
(Conditions)

A reaction solution was prepared so that the total amount was 10 μL per one reaction. The reaction solution contained the first nucleic acid (1 μM), the fourth nucleic acid (2 μM), 3-morpholinopropanesulfonic acid (pH 7.9, 10 mM), $MgCl_2$ (10 mM), Tween 20 (0.05% v/v), flap endonuclease 1 (0.03 mg/mL) as a second nucleic acid cleavage enzyme and distilled water.

(Procedure)

The reaction solution was charged into a micro test tube and heated at 65° C. for 60 minutes in a real-time PCR device. Change in fluorescence intensity (excitation: 490 nm, luminescence: 520 nm) during the heating was measured.

(Results)

Figure 12:
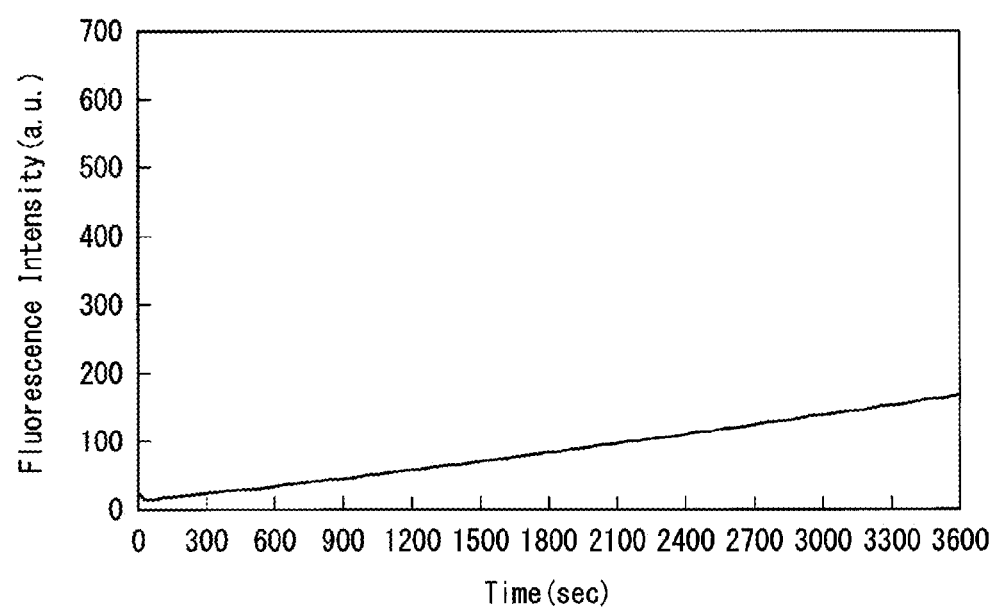
FIG. 12 is a graph showing change in fluorescence intensity with time observed in an example.

FIG. 12 shows the results. In the absence of the target RNA, it was observed that fluorescence intensity increased with time. However, compared to FIG. 11, it was confirmed that the contribution to noise was small. From these results as well, it was confirmed that at least the first and fourth nucleic acids contributed to increasing noise (fluorescence intensity increased in the absence of the target RNA).

Elements that affect the increase of noise are the first and fourth nucleic acids and enzymes, and the first nucleic acid cleavage enzyme has a larger influence than does the second nucleic acid cleavage enzyme. The amount of the first nucleic acid cleavage enzyme may be simply increased to reduce time required for detecting a target nucleic acid. Contrarily, however, decrease in the amount of the first nucleic acid cleavage enzyme can raise the signal/noise ratio at the time of detection and the target nucleic acid can be more effectively detected. Mixing of the second nucleic acid cleavage enzyme can also prevent the increase of detection time.

Some preferred embodiments of the present invention have been described so far, but the present invention should not be limited to the embodiments described above. Addition, omission, substitution, and other modifications of the configuration can be made without departing from the spirit of the invention.

The present application addresses the following. The method in which the reaction vessel is opened halfway through is cumbersome and has a high risk of inducing false positives due to sample contamination from outside. Consequently, accuracy of the test may be impaired. Therefore, when prompt and accurate RNA detection is required to be conducted, it is desired to use a method enabling easy operation, maintaining cleavage activity in a reaction system where both structures are mixed, and minimizing side reactions.

The present invention has an aspect to provide a method of promptly detecting RNA.

A method of detecting a nucleic acid according to one embodiment of the present invention is used for detecting a target nucleic acid in a fluid that contains the target nucleic acid. The method includes a detection reagent mixing step of mixing a detection reagent into the fluid, the detection reagent containing a first nucleic acid cleavage enzyme and a second nucleic acid cleavage enzyme. In the method, a first flap is cleaved by the first nucleic acid cleavage enzyme to produce a third nucleic acid, the first flap being associated with a first invasive structure that is a complex formed by the target nucleic acid, a first nucleic acid having the first flap and a second nucleic acid; and a second flap is cleaved by the second nucleic acid cleavage enzyme to produce a cleaved product, the second flap being associated with a second invasive structure that is a complex formed on a fifth nucleic acid by the third nucleic acid and a fourth nucleic acid having the second flap.

The problem can be solved by any of the following (1) to (20).

(1) A method of detecting a nucleic acid, the method being used for detecting a target nucleic acid in a fluid that contains the target nucleic acid, including a detection reagent mixing step of mixing a detection reagent into the fluid, the detection reagent containing a first nucleic acid cleavage enzyme and a second nucleic acid cleavage enzyme, wherein a first flap is cleaved by the first nucleic acid cleavage enzyme to produce a third nucleic acid, the first flap being associated with a first invasive structure that is a complex formed by the target nucleic acid, a first nucleic acid having the first flap and a second nucleic acid; and a second flap is cleaved by the second nucleic acid cleavage enzyme to produce a cleaved product, the second flap being associated with a second invasive structure that is a complex formed by the third nucleic acid and a fourth nucleic acid having the second flap.

(2) The method of detecting a nucleic acid according to (1), wherein the target nucleic acid is RNA; and at least the first flap of the first nucleic acid, the second nucleic acid and the fourth nucleic acid contain DNA.

(3) The method of detecting a nucleic acid according to (1), wherein the target nucleic acid and the fourth nucleic acid are DNA, and the first nucleic acid and the second nucleic acid contain RNA.

(4) The method of detecting a nucleic acid according to any one of (1) to (3), wherein the third nucleic acid, the fourth nucleic acid having the second flap and a fifth nucleic acid form a complex to provide the second invasive structure; and the fifth nucleic acid contains DNA.

(5) The method of detecting a nucleic acid according to any one of (1) to (4), wherein cleavage activity of the second nucleic acid cleavage enzyme for the first invasive structure is lower than cleavage activity of the first nucleic acid cleavage enzyme for the first invasive structure; and cleavage activity of the first nucleic acid cleavage enzyme for the second invasive structure is lower than cleavage activity of the second nucleic acid cleavage enzyme for the second invasive structure.

(6) The method of detecting a nucleic acid according to (4), wherein cleavage activity of the second nucleic acid cleavage enzyme for the first invasive structure is 90% or less of cleavage activity of the first nucleic acid cleavage enzyme for the first invasive structure; and cleavage activity of the first nucleic acid cleavage enzyme for the second invasive structure is 90% or less of cleavage activity of the second nucleic acid cleavage enzyme for the second invasive structure.

(7) The method of detecting a nucleic acid according to any one of (1) to (6), wherein cleavage activity of the first nucleic acid cleavage enzyme for the fourth nucleic acid is lower than cleavage activity of the second nucleic acid cleavage enzyme for the second invasive structure.

(8) The method of detecting a nucleic acid according to any one of (1) to (7), wherein cleavage activity of the first nucleic acid cleavage enzyme for the fourth nucleic acid and cleavage activity of the second nucleic acid cleavage enzyme for the fourth nucleic acid are lower than cleavage activity of the first nucleic acid cleavage enzyme for the first invasive structure and cleavage activity of the second nucleic acid cleavage enzyme for the second invasive structure.

(9) The method of detecting a nucleic acid according to (8), wherein cleavage activity of the first nucleic acid cleavage enzyme for the fourth nucleic acid and cleavage activity of the second nucleic acid cleavage enzyme for the fourth nucleic acid are 80% or less of cleavage activity of the first nucleic acid cleavage enzyme for the first invasive structure and cleavage activity of the second nucleic acid cleavage enzyme for the second invasive structure.

(10) The method of detecting a nucleic acid according to any one of (1) to (9), wherein a concentration of the first nucleic acid cleavage enzyme is 9 times or less of a concentration of the second nucleic acid cleavage enzyme.

(11) The method of detecting a nucleic acid according to any one of (1) to (10), wherein a concentration of the first nucleic acid cleavage enzyme is 0.27 mg/mL or less.

(12) The method of detecting a nucleic acid according to any one of (1) to (11), wherein a concentration of the second nucleic acid cleavage enzyme is 0.12 mg/mL or less.

(13) The method of detecting a nucleic acid according to any one of (1) to (12), wherein the method further includes a target nucleic acid confirmation step in which at least one of the first nucleic acid and the fourth nucleic acid forming an invasive structure is fluorescently labeled, and cleavage of the invasive structure is detected according to change in fluorescence intensity.

(14) The method of detecting a nucleic acid according to any one of (1) to (12), wherein the method further includes a target nucleic acid confirmation step of detecting the cleaved product by comparing migration degrees before and after reactions by using electrophoresis.

(15) The method of detecting a nucleic acid according to (13) wherein production of the cleaved product by the first nucleic acid cleavage enzyme and the second nucleic acid cleavage enzyme in the detection reagent mixing step is performed in microspaces.

(16) The method of detecting a nucleic acid according to (15) wherein the microspaces each have a height of 10 nm to 100 μm.

(17) The method of detecting a nucleic acid according to (15) or (16) wherein the microspaces are provided at a density of 100,000/cm$^2$ to 10,000,000/cm$^2$.

(18) The method of detecting a nucleic acid according to any one of (15) to (17), wherein, the target nucleic acid is detected in the target nucleic acid confirmation step by detecting the cleaved product produced in the microspaces.

(19) The method of detecting a nucleic acid according to any one of (1) to (18), wherein the first nucleic acid cleavage enzyme is 5'-nuclease and the second nucleic acid cleavage enzyme is FEN-1.

(20) A detection reagent for performing the method of detecting a nucleic acid according to any one of (1) to (19), wherein the detection reagent contains the first nucleic acid cleavage enzyme and the second nucleic acid cleavage enzyme.

According to an embodiment of the present invention, a method of detecting a nucleic acid can be provided for prompt detection of a target nucleic acid, e.g., RNA, in a fluid containing the target nucleic acid, and can provide a detection reagent for performing the method of detecting a nucleic acid.

INDUSTRIAL APPLICABILITY

According to an embodiment of the present invention, a method of detecting a nucleic acid can be provided for prompt detection of a target nucleic acid in a fluid containing the target nucleic acid, and can provide a detection reagent for performing the method of detecting a nucleic acid.

REFERENCE SIGNS LIST

1 Microfluidic device
3 Well (microspace)
4 Microwell array
5 Cover member
6 Aperture surface
7 Perimeter region
8 Well-forming region
9 Bottom
15 Through hole
15A First through hole
15B Second through hole
16 Small through hole
17 Large through hole
20 Fluid
23 Detection reagent (microdroplet)

Obviously, numerous modifications and variations of the present invention are possible in light of the above teachings. It is therefore to be understood that within the scope of the appended claims, the invention may be practiced otherwise than as specifically described herein.

What is claimed is:

1. A method of detecting a nucleic acid, comprising:
preparing a detection reagent comprising a first enzyme and a second enzyme, wherein the first enzyme is a 5'-nuclease, and the second enzyme is FEN-1 such that a concentration of the first enzyme is in a range of 0.63 times to 2.46 times a concentration of the second enzyme;
mixing, with the detection reagent, a fluid comprising a target nucleic acid, a first nucleic acid having a first flap, a second nucleic acid, and a fourth nucleic acid having a second flap such that a cleaved product is produced, wherein the cleavage activity of the second enzyme for a first invasive structure is lower than the cleavage activity of the first enzyme for the first invasive structure, the cleavage activity of the first enzyme for a second invasive structure is lower than the cleavage activity of the second enzyme for the second invasive structure, the mixing comprises a first reaction in which the first nucleic acid forms a complex comprising the first invasive structure having the first flap with the target nucleic acid and the second nucleic acid, and the first enzyme cleaves the first flap of the first invasive structure and produces a third nucleic acid, and a second reaction in which the third nucleic acid forms a complex comprising the second invasive structure having the second flap with the fourth nucleic acid, and the second enzyme cleaves the second flap of the second invasive structure and produces the cleaved product; and
detecting the cleaved product such that the target nucleic acid is detected, wherein the fluid is mixed with the detection reagent such that the concentration of the first enzyme is 0.27 mg/mL or less and the concentration of the second enzyme is 0.12 mg/mL or less.

2. The method according to claim 1, wherein the target nucleic acid is RNA, and at least the first flap of the first nucleic acid, the second nucleic acid and the fourth nucleic acid include DNA.

3. The method according to claim 1, wherein the target nucleic acid and the fourth nucleic acid are DNAs, and the first nucleic acid and the second nucleic acid include RNA.

4. The method according to claim 1, wherein the fluid comprises a fifth nucleic acid, and the second invasive structure is a complex formed by the third nucleic acid, the fourth nucleic acid and the fifth nucleic acid, and the fifth nucleic acid includes DNA.

5. The method according to claim 1, wherein the cleavage activity of the second enzyme for the first invasive structure is more than 0% and 90% or less relative to the cleavage activity of the first enzyme for the first invasive structure, and the cleavage activity of the first enzyme for the second invasive structure is more than 0% and 90% or less relative to the cleavage activity of the second enzyme for the second invasive structure.

6. The method according to claim 5, wherein the cleavage activity of the second enzyme for the first invasive structure is 80% or less relative to the cleavage activity of the first enzyme for the first invasive structure, and the cleavage activity of the first enzyme for the second invasive structure is 80% or less relative to the cleavage activity of the second enzyme for the second invasive structure.

7. The method according to claim 1, wherein the cleavage activity of the first enzyme for the fourth nucleic acid is lower than the cleavage activity of the second enzyme for the second invasive structure.

8. The method according to claim 1, wherein the cleavage activity of the first enzyme for the fourth nucleic acid and the cleavage activity of the second enzyme for the fourth nucleic acid are lower than the cleavage activity of the first enzyme for the first invasive structure and cleavage activity of the second enzyme for the second invasive structure.

9. The method according to claim 8, wherein the cleavage activity of the first enzyme for the fourth nucleic acid and the cleavage activity of the second enzyme for the fourth nucleic acid are 80% or less of the cleavage activity of the first enzyme for the first invasive structure and the cleavage activity of the second enzyme for the second invasive structure.

10. The method according to claim 1, wherein the fluid is mixed with the detection reagent such that the concentration of the first enzyme is in a range of 0.63 times to 1.23 times the concentration of the second enzyme.

11. The method according to claim 1, wherein the fluid is mixed with the detection reagent such that a concentration of the first enzyme is 0.18 mg/mL or less.

12. The method according to claim 1, wherein the fluid is mixed with the detection reagent such that a concentration of the second enzyme is 0.06 mg/mL or less.

13. The method according to claim 1, further comprising:
detecting cleavage of at least one of the first and second invasive structures by detecting a change in fluorescence intensity,
wherein the first nucleic acid and/or the fourth nucleic acid are fluorescently labeled.

14. The method according to claim 1, further comprising:
detecting the cleaved product by comparing migration degrees before and after the second reaction by electrophoresis.

15. The method according to claim 13, wherein the cleaved product is produced in a plurality of microspaces.

16. The method according to claim 15, wherein the microspaces each have a height in a range of 10 nm to 100 µm.

17. The method according to claim 15, wherein the microspaces are formed at a density in a range of 100,000/cm$^2$ to 10,000,000/cm$^2$.

18. The method according to claim 15, wherein the target nucleic acid is detected by detecting the cleaved product produced in the microspaces.

19. The method according to claim 1, wherein the fluid is mixed with the detection reagent such that the concentration of the first enzyme is less than 0.18 mg/mL and the concentration of the second enzyme is 0.06 mg/mL or less.

20. The method according to claim 5, wherein the cleavage activity of the first enzyme for the fourth nucleic acid and the cleavage activity of the second enzyme for the fourth nucleic acid are lower than the cleavage activity of the first enzyme for the first invasive structure and the cleavage activity of the second enzyme for the second invasive structure.

* * * * *